(12) United States Patent
Hipwood et al.

(10) Patent No.: US 11,707,870 B2
(45) Date of Patent: Jul. 25, 2023

(54) REEL BASED CLOSURE SYSTEM

(71) Applicant: Boa Technology Inc., Denver, CO (US)

(72) Inventors: Daniel Hipwood, Englewood, CO (US);
Eric Irwin, Denver, CO (US); Thomas Trudel, Denver, CO (US); Mark Soderberg, Conifer, CO (US); Michael Nickel, Golden, CO (US); Oronde Armstrong, Denver, CO (US); Cody Henderson, Denver, CO (US); Greg Langley, Denver, CO (US); William Roushey, Denver, CO (US); Thomas Pollack, Golden, CO (US); Ashley Pickens, Evergreen, CO (US); Ilya Minkin, Denver, CO (US); Eric Whewell, Denver, CO (US)

(73) Assignee: BOA TECHNOLOGY, INC., Denver, CO (US)

( * ) Notice: Subject to any disclaimer, the term of this patent is extended or adjusted under 35 U.S.C. 154(b) by 24 days.

(21) Appl. No.: 17/521,189

(22) Filed: Nov. 8, 2021

(65) Prior Publication Data
US 2022/0055271 A1 Feb. 24, 2022

Related U.S. Application Data

(63) Continuation of application No. 16/709,451, filed on Dec. 10, 2019, now Pat. No. 11,220,030, which is a
(Continued)

(51) Int. Cl.
*B29C 45/14* (2006.01)
*A61F 5/01* (2006.01)
(Continued)

(52) U.S. Cl.
CPC ........ *B29C 45/14786* (2013.01); *A43C 11/00* (2013.01); *A43C 11/165* (2013.01);
(Continued)

(58) Field of Classification Search
CPC ......... B29C 45/14786; B29C 45/14311; B29C 2045/14327; A43C 11/00; A43C 11/165;
(Continued)

(56) References Cited

U.S. PATENT DOCUMENTS 2,775,417 A * 12/1956 Freund .................. A01K 89/01
242/282
9,259,056 B2 2/2016 Soderberg et al.
(Continued)

FOREIGN PATENT DOCUMENTS

AT          517092 A4    11/2016
JP        2010-42639 A    2/2010
JP        2015-516828 T   6/2015

*Primary Examiner* — David M Upchurch
(74) *Attorney, Agent, or Firm* — Kilpatrick Townsend & Stockton LLP

(57) ABSTRACT

A reel based tensioning device includes a housing, a spool that is rotatably positioned within the housing, and a knob member that is operably coupled with the spool to cause the spool to rotate in a first direction within the housing and thereby wind a tension member about the spool. The reel based tensioning device also includes a load holding mechanism that is coupled with the spool and that is configured to rotate the spool in the first direction within the housing and to prevent rotation of the spool in a second direction to prevent unwinding of the tension member from about the spool. The reel based tensioning device further includes an audible component that is configured to produce an audible noise responsive to operation of the knob member to signal an adjustment of the tension member.

20 Claims, 20 Drawing Sheets

Related U.S. Application Data continuation of application No. 15/907,077, filed on Feb. 27, 2018, now Pat. No. 10,543,630.

(60) Provisional application No. 62/465,342, filed on Mar. 1, 2017, provisional application No. 62/464,050, filed on Feb. 27, 2017.

(51) Int. Cl.
| | |
|---|---|
| *A43C 11/16* | (2006.01) |
| *A43C 11/00* | (2006.01) |
| *A43C 11/10* | (2006.01) |
| *B29L 31/50* | (2006.01) |
| *B29K 23/00* | (2006.01) |
| *B29K 67/00* | (2006.01) |
| *B29K 509/08* | (2006.01) |
| *B29L 31/00* | (2006.01) |

(52) U.S. Cl.
CPC .......... *A61F 5/01* (2013.01); *B29C 45/14311* (2013.01); *B29C 2045/14327* (2013.01); *B29K 2023/12* (2013.01); *B29K 2067/00* (2013.01); *B29K 2509/08* (2013.01); *B29L 2031/508* (2013.01); *B29L 2031/727* (2013.01)

(58) Field of Classification Search
CPC ... A61F 5/01; B29K 2023/12; B29K 2067/00; B29K 2509/08; B29L 2031/508; B29L 2031/727

See application file for complete search history.

(56) References Cited

U.S. PATENT DOCUMENTS

| | | | |
|---|---|---|---|
| 9,770,070 B2 | 9/2017 | Cotterman et al. | |
| 2003/0204938 A1* | 11/2003 | Hammerslag | A43C 11/004 |
| | | | 24/68 SK |
| 2007/0169378 A1* | 7/2007 | Sodeberg | A45C 7/0063 |
| | | | 36/50.5 |
| 2008/0172848 A1 | 7/2008 | Chen | |
| 2010/0139057 A1* | 6/2010 | Soderberg | A61F 5/0118 |
| | | | 242/396.2 |
| 2010/0299959 A1* | 12/2010 | Hammerslag | A43C 11/16 |
| | | | 36/50.5 |
| 2013/0092780 A1 | 4/2013 | Soderberg et al. | |
| 2014/0221889 A1 | 8/2014 | Burns et al. | |
| 2014/0359981 A1 | 12/2014 | Cotterman et al. | |
| 2015/0007422 A1* | 1/2015 | Cavanagh | A43C 11/165 |
| | | | 29/434 |
| 2016/0044994 A1 | 2/2016 | Soderberg et al. | |
| 2016/0120267 A1* | 5/2016 | Burns | A44B 11/065 |
| | | | 24/68 C |
| 2017/0027287 A1 | 2/2017 | Burns et al. | |

\* cited by examiner

REEL BASED CLOSURE SYSTEM

CROSS-REFERENCE TO RELATED APPLICATIONS

This application is a continuation of U.S. patent application Ser. No. 16/709,451 filed Dec. 10, 2019, entitled "Reel Based Closure System Employing Friction Based Tension Mechanism" which is a continuation of U.S. patent application Ser. No. 15/907,077 filed Feb. 27, 2018, entitled "Reel Based Closure System Employing Friction Based Tension Mechanism" which claims the benefit and priority to Provisional U.S. Patent Application No. 62/465,342 filed Mar. 1, 2017, entitled "Reel Based Closure System Employing Friction Based Tension Mechanism" and Provisional U.S. Patent Application No. 62/464,050 filed Feb. 27, 2017, entitled "Reel Based System With Magnetic Coupling Mechanism," the entire disclosures of which are hereby incorporated by reference, for all purposes, as if fully set forth herein.

BACKGROUND OF THE INVENTION

The present disclosure is related to reel based closure devices for various articles, such as braces, medical devices, shoes, clothing, apparel, and the like. Such articles typically include some closure system, which allows the article to be placed about a body part and closed or tightened about the body part. The closure systems are typically used to maintain or secure the article about the body part. For example, shoes are typically placed over an individual's foot and the shoelace is tensioned and tied to close and secure the shoe about the foot. Conventional closure systems have been modified in an effort to increase the fit and/or comfort of the article about the body part. For example, shoe lacing configurations and/or patterns have been modified in an attempt to increase the fit and/or comfort of wearing shoes. Conventional closure systems have also been modified in an effort to decrease the time in which an article may be closed and secured about the body part. These modifications have resulted in the use of various pull cords, straps, and tensioning devices that enable the article to be quickly closed and secured to the foot.

BRIEF DESCRIPTION OF THE INVENTION

The embodiments described herein provide reel based tensioning devices, and components therefor, that may be used to tension a lace or tension member and thereby tighten an article or other item. According to one aspect, an insert molded component for a reel based tensioning device includes a base member of a reel based tensioning device and a fabric material. The base member is typically made of a polymer material and includes a top end and a bottom end with a bottom surface. The base member has an interior cavity within which one or more components of the reel based tensioning device are positionable. The fabric material is substantially flush with the bottom surface of the base member and extends laterally from at least a portion of an outer periphery of the bottom end of the base member. The base member is insert molded onto the fabric material by injecting the polymer material through the fabric material so that when the insert molded component is formed, the fabric material is disposed within at least a portion of the base member with the polymer material of the least a portion of the base member being disposed on opposite sides of the fabric material.

According to another aspect, a component of a reel based tensioning system includes a first component that is made of a polymer material and that includes a top end, a bottom end, and an interior cavity within which a second component of the reel based tensioning system is positionable. The component also includes a fabric material that is positioned near the bottom end of the first component and that extends laterally from at least a portion of an outer periphery of the first component. The fabric material is integrally coupled with the first component by injecting the polymer material of the first component through the fabric material so that the polymer material of at least a portion of the first component is saturated or impregnated through the fabric material and so that the polymer material of the at least a portion of the first component extends axially bellow a bottom surface of the fabric material and axially above a top surface of the fabric material.

According to another aspect, a method of forming a component of a reel based tensioning system includes providing a fabric material, positioning the fabric material within a die or mold, and injecting a polymer material through the fabric material so that the polymer material fills a void or space within the die or mold that defines a shape of a first component of the reel based tensioning system. The method also includes cooling the polymer material so that the polymer material hardens and forms the first component of the reel based tensioning system. The polymer material of at least a portion of the first component is saturated or impregnated through the fabric material so that the polymer material of the at least a portion of the first component extends axially bellow a bottom surface of the fabric material and axially above a top surface of the fabric material.

According to another aspect, a reel based tensioning device includes a housing having an interior region and a spool positioned within the interior region of the housing and rotatable relative thereto. The reel based tensioning device also includes a knob member that is operably coupled with the spool to cause the spool to rotate in a first direction within the interior region of the housing to wind a tension member about the spool and thereby tension the tension member. The reel based tensioning device further includes a load holding mechanism that is coupled with the spool and that is configured to allow rotation of the spool in the first direction within the interior region of the housing and to prevent rotation of the spool in a second direction within the interior region of the housing to prevent unwinding of the tension member from about the spool. The reel based tensioning device additionally includes an audible component that is separate from the load holding mechanism and that is configured to produce an audible noise in response to operation of the knob member to audibly signal an adjustment in tension of the tension member.

According to another aspect, a reel based tensioning device includes a housing, a spool rotatably positioned within the housing, a knob member that is operably coupled with the spool to cause the spool to rotate in a first direction within the housing to wind a tension member about the spool, a load holding mechanism that is coupled with the spool and configured to allow rotation of the spool in the first direction within the housing and to prevent rotation of the spool in a second direction within the housing to prevent unwinding of the tension member from about the spool, and an audible component that is configured to produce an audible noise responsive to operation of the knob member to signal an adjustment of the tension member.

According to another aspect, a method of configuring a reel based tensioning device includes providing the reel based tensioning device, in which the reel based tensioning device includes a housing, a spool rotatably positioned within the housing, a knob member that is operably coupled with the spool to cause the spool to rotate in a first direction within the housing to wind a tension member about the spool, and a load holding mechanism that is coupled with the spool and that is configured to allow rotation of the spool in the first direction within the housing and to prevent rotation of the spool in a second direction within the housing to prevent unwinding of the tension member from about the spool. The method also includes coupling an audible component with the reel based tensioning device, in which the audible component is configured to produce an audible noise responsive to operation of the knob member to signal an adjustment of the tension member.

According to another aspect, a reel based tensioning device for tightening an article includes a housing having an interior region, a spool positioned within the interior region of the housing and rotatable relative thereto, a knob member that is operably coupled with the spool to cause the spool to rotate within the interior region of the housing, and a load holding mechanism that is coupled with the spool. The load holding mechanism includes a spring that frictionally engages with a cylindrical member to prevent rotation of the spool within the interior region of the housing responsive to forces imparted on the spool from a source other than the knob member, such as tension in the tension member that imparts a rotational force on the spool. The knob is operationally coupled with the load holding mechanism so that a rotation of the knob in a first direction reduces the frictional engagement of the spring and cylindrical member in order to allow rotation of the spool in the first direction within the interior region of the housing and thereby wind a tension member about the spool. The knob is also operationally coupled with the load holding mechanism so that a rotation of the knob in a second direction also reduces the frictional engagement of the spring and cylindrical member in order to allow rotation of the spool in the second direction within the interior region of the housing and thereby unwind the tension member from about the spool.

According to another aspect, a reel based tensioning device includes a housing, a spool that is rotatably positioned within the housing, a knob member that is operably coupled with the spool to cause the spool to rotate within the housing, and a load holding mechanism that includes a spring that frictionally engages with a cylindrical member to prevent unwanted rotation of the spool within the housing. The knob member is operationally coupled with the load holding mechanism so that a first operation of the knob member reduces the frictional engagement of the spring and cylindrical member to allow rotation of the spool within the housing to wind a tension member about the spool and so that a second operation of the knob member also reduces the frictional engagement of the spring and cylindrical member to allow rotation of the spool within the housing to unwind the tension member from about the spool.

According to another aspect, a method for assembly an article with a reel based tensioning device includes providing a reel based tensioning device, in which the reel based tensioning device includes a housing, a spool that is rotatably positioned within the housing, a knob member that is operably coupled with the spool to cause the spool to rotate within the housing, and a load holding mechanism that includes a spring that frictionally engages with a cylindrical member to prevent unwanted rotation of the spool within the housing. The knob member is operationally coupled with the load holding mechanism so that a first operation of the knob member reduces the frictional engagement of the spring and cylindrical member to allow rotation of the spool within the housing to wind a tension member about the spool and a second operation of the knob member also reduces the frictional engagement of the spring and cylindrical member to allow rotation of the spool within the housing to unwind the tension member from about the spool. The method also includes coupling the reel based tensioning device member with the article.

BRIEF DESCRIPTION OF THE DRAWINGS

The present invention is described in conjunction with the appended figures.

Figure 1:
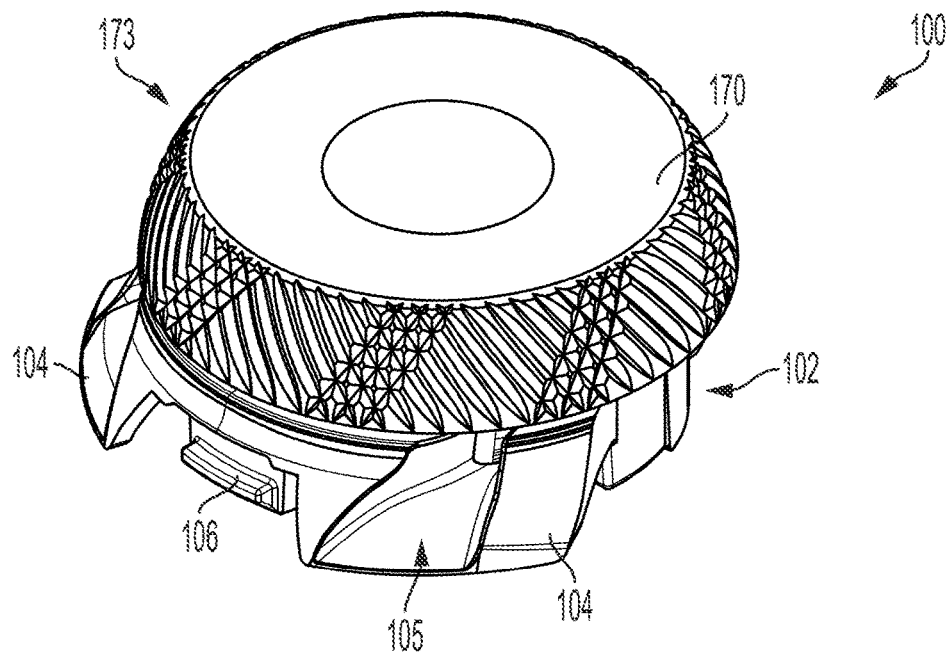
FIG. 1 illustrates a perspective view of an assembled reel system showing a knob attached to a housing, which is typically coupled with a base member.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

The embodiments herein describe reel based closure or tensioning devices that may be used to tension a lace or tension member and thereby tighten an article or other item. The reel based tensioning devices are also referred to herein as reel systems or simply closure devices. The article may be a variety of items including a pack (i.e., back pack, book bag, etc.), an article of clothing (i.e., hats, gloves, belt, etc.), sports apparel (boots, snowboard boots, ski boots, etc.), medical braces (i.e., back braces, knee braces, wrist brace, ankle brace, etc.), and/or various other items or apparel. A specific embodiment in which the closure system may be employed involves footwear, such as shoes, boots, sandals, etc.

The reel systems herein employ friction based tension adjustment mechanisms, which are used to tension a lace, cord, or tension member (hereinafter tension member) and to maintain the tension of the tension member. The friction based tension adjustment mechanisms described herein employ a load holding mechanism having a spring (e.g., a coil spring) that frictionally engages with a cylindrical member, such as a boss or hub, in order to provide a load holding function that maintains the tension in the tension member. Specifically, the frictional engagement of the spring and the cylindrical member is employed to prevent unwanted rotation of a spool within the housing. Since the reel systems are used to maintain tension in the tension member, unwanted rotation of the spool means any rotation of the spool that is not initiated by a user and that would result in loosening or un-tensioning of the tension member. Stated differently, the system is designed so that the spool will rotate only in response to an action by the user to loosen or un-tension the lace, which commonly involves a rotation of a knob component of the reel system in a loosening direction, but could also involve other actions, such as operating a lever, pressing a button, pulling axially upward on the knob, and the like. Absent this action by the user, the spring and the cylindrical member are designed to frictionally engage and prevent rotation of the spool within the housing.

The reel system typically includes a knob that is designed to be grasped and rotated by a user. The knob member is operationally coupled with the load holding mechanism so that a first operation of the knob member (e.g., rotation of the knob in a tightening direction) reduces the frictional engagement of the spring and cylindrical member to allow rotation of the spool within the housing to wind the tension member about the spool. The knob member is also operationally coupled with the load holding mechanism so that a second operation of the knob member (e.g., rotation of the knob in a loosening direction) reduces the frictional engagement of the spring and cylindrical member to allow rotation of the spool within the housing to unwind the tension member from about the spool.

In an exemplary embodiment, the coil spring is positioned or wound about an exterior of a hub member or central cylindrical boss. The coil spring is configured to constrict about the hub member or central cylindrical boss in order to provide the load holding function. In one embodiment, the hub member or central cylindrical boss may include an upper hub member that is fixedly secured to the spool and a lower hub member that is fixedly secured to the housing. The upper hub member may have a diameter that is slightly larger than a diameter of the lower hub member. In such embodiments, a distal end of the upper hub member that interfaces with the lower hub member may be tapered. In another embodiment, the hub member or central cylindrical boss may be an inner hub member and the reel system may also include an outer hub member that is disposed over the inner hub member and that is operationally coupled with the knob member and the spring so that a rotation of the knob member in a loosening direction reduces the frictional engagement of the spring and the inner hub member. In such embodiments, the outer hub member may be coupled with the knob member such that rotation of the knob member in the loosening direction effects a rotation of the outer hub in the loosening direction. The spring may include a tang that is coupled with the outer hub member so that rotation of the outer hub member in the loosening direction effects a widening of a diameter of the spring thereby reducing the frictional engagement of the spring and the inner hub member. In yet another embodiment, the coil spring may be positioned within a cylindrical channel or recess of a boss or hub. In such embodiments, the coil spring is biased to flex radially outward and into frictional engagement with an interior wall of the cylindrical channel or recess in order to provide the load holding function.

The friction based tension adjustment mechanism eliminates the need for pawls or flexible arms that are commonly used in conventional systems to provide the load holding functions. In such conventional systems, a pawl or arm commonly engages with teeth in order to provide the load holding function. The pawl/arm and teeth are often sloped or configured to enable a one-way motion of the pawl/arm and thereby the reel based device, such as rotation of a knob in a tightening direction. The pawl/arm and teeth lockingly engage when the knob is rotated in an opposite direction in order to prevent rotation of one or more components of the system that would loosen the tension in the tension member. The embodiments herein may be entirely free of a pawl or arm that functions to provide load holding capabilities. In other embodiments, the reel system may include a combination of a friction based mechanism and a pawl or arm in order to provide the load holding functions.

The load holding mechanism described herein (i.e., the spring and hub member) may not produce an audible noise that is detectable by a human ear. As such, the reel system may include an audible component that is configured to produce an audible noise responsive to operation of the knob member to signal an adjustment of the tension member. The audible component may be configured to produce an audible noise responsive to tensioning of the tension member and to produce an audible noise responsive to loosening of the tension member. The audible noise that is produced responsive to tensioning of the tension member may be different than the audible noise responsive to loosening of the tension member. The audible component may be coupled with a top surface of the spool.

While the systems herein are commonly devoid of a load holding pawl or arm, in the exemplary embodiment, a separate pawl system, member, or beam may be used to produce the audible noise or sound when the system is operated. For example, the pawl system, member, or beam may be used primarily to produce a click sound when the knob is rotated, which audibly indicates to a user that the system is being used to tension or loosen the tension member. The pawl system, member, or beam may provide audible feedback that users of the system may expect and/or desire. The pawl system, member, or beam may be incapable of preventing rotation of the spool within the housing when an appreciable rotational force is imposed on the spool via the tension member or knob member. For example, when the user rotates the knob member in a loosening direction, the pawl system, member, or beam may not appreciably impede the rotation of the knob member.

Additional features and aspects of the reel based closure devices will be evident with references to the description of the several drawings which is provided herein below.

Figure 16:
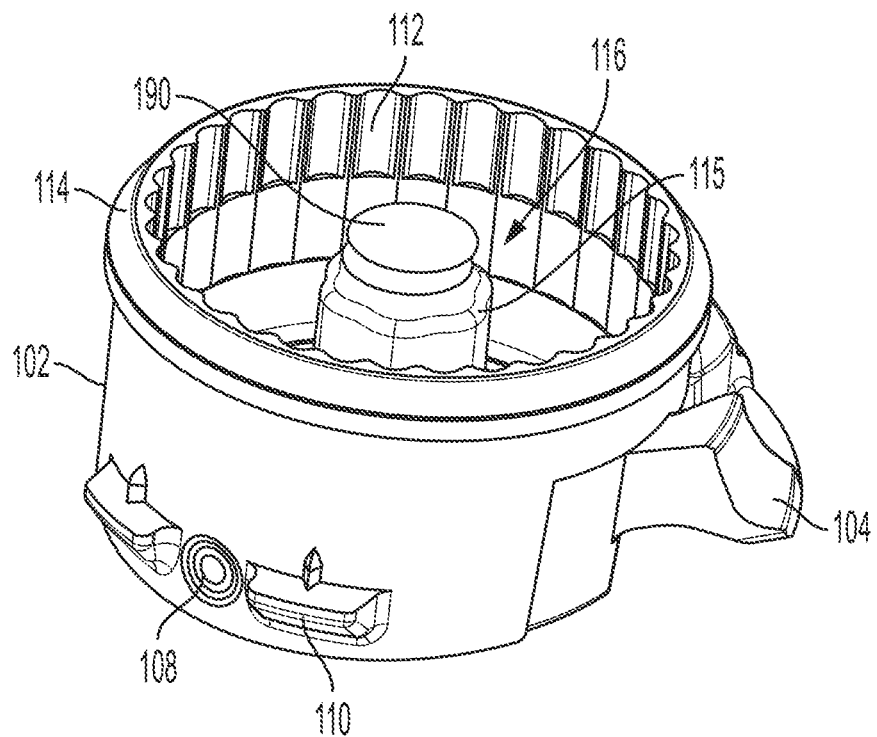
FIG. 16 illustrates a housing of the reel system of FIG. 1 and various features of the housing.
Figure 17:
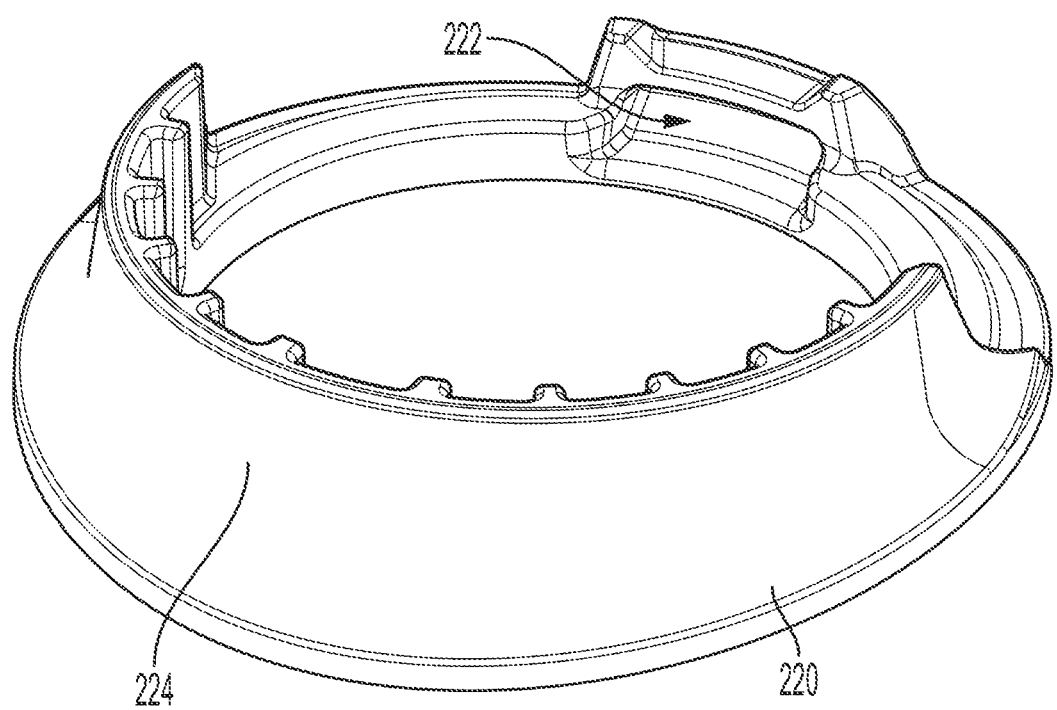

FIG. 1 illustrates an assembled perspective view of the reel system 100. The assembled reel system 100 shows a knob 170 attached to a housing 102, which is typically coupled with a base member 220. The housing 102 is coupled with the base member 220 in a manner that allows the housing 102 to be detached or removed from the base member 220. Coupling of the housing 102 and base member is achieved via engagement of mating features that are positioned on both components. FIG. 1 illustrates a lip or flange member 106 that is positionable within a front tab 222 of the base member 220 to couple the front portion of the housing 102 to the base member 220. FIG. 16 illustrates tabs 110 that are positioned on an opposite side of the housing 102. The tabs 110 are designed to fit within corresponding slots on an interior surface of a wall 224 that partially surrounds the periphery of the base member 220. FIG. 16 also illustrates lace ports 104 of the housing 102. The lace ports include an opening 105 within which the tension member is inserted to allow the tension member to access the interior of the housing 102. As illustrated in FIG. 17, the base member 220 includes open portions or areas on opposing sides of the front tab 222 that are shaped and sized to accommodate the lace ports 104, which provides a visual appearance of the base member 220 and housing 102 being a unitary component.

The housing 102 is shaped so that it corresponds with an outer surface of the base member 220 and with the outer surface of the knob 170. For example, when the housing 102 is attached to the base member 220, the outer surfaces of these components align so that they appear as a continuous or matching surface. The matching outer surfaces of the housing 102 and the base member 220 helps to conceal or hide the edges of both components. In this manner, the user does not readily perceive the separate edges of the components, but rather visually perceives the separate components as an integral unit. The outer surface of the housing 102 similarly aligns with the knob 170 so that the outer surfaces appear to flow together. The alignment of the knob 170 and outer surface of the housing 102 also eliminates or minimizes ridges or edges that could catch on surrounding objects and open the system or separate the knob 170 from the housing 102. The shape of the housing 102, knob 170, and base member 220 provides a visually appealing look that users may desire.

The knob 170 is coupled with the housing 102 via a snap engagement or fit. Specifically, an inner surface of the knob 170 include radially inwardly protruding tabs 176 that are configured to snap over a radially outwardly protruding rib 114 of the housing 102. The knob 170 may flex radially outward slightly as the two components are snap fit together. The snap fit engagement or coupling allows the components to be attached together without the use of a screw, bolt, or other similar mechanical fastener. An exemplary embodiment of a snap fit coupling of a knob and housing is further described in U.S. patent application Ser. No. 14/297,047, filed Jun. 5, 2014, and entitled "Integrated Closure Device Components and Methods," the entire disclosure of which is incorporated by reference herein.

Figure 5:
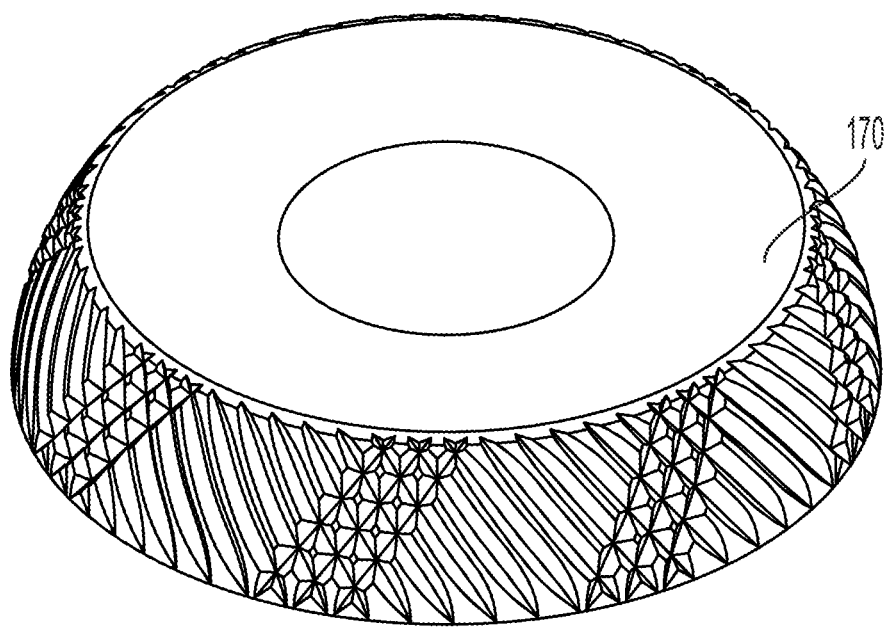
FIG. 5 illustrates a perspective view of a knob member of the reel system of FIG. 1.

FIGS. 1 and 5 illustrate the knob 170 having a textured or patterned outer rim 173, which in some instances may have a knurled configuration. The textured or patterned outer rim may enhance the grip surface of the rim 173 of the knob 170 and/or may be employed for aesthetic appeal. In some instances, the knob 170 may be made of a metal material, such as aluminum or stainless steel. In such instances, the textured or patterned outer rim 173 may significantly enhance the grip properties of the knob 170. In other instances, the knob 170 may be made of plastic materials, such as polypropylene, polyethylene, nylon, and the like.

Figure 2:
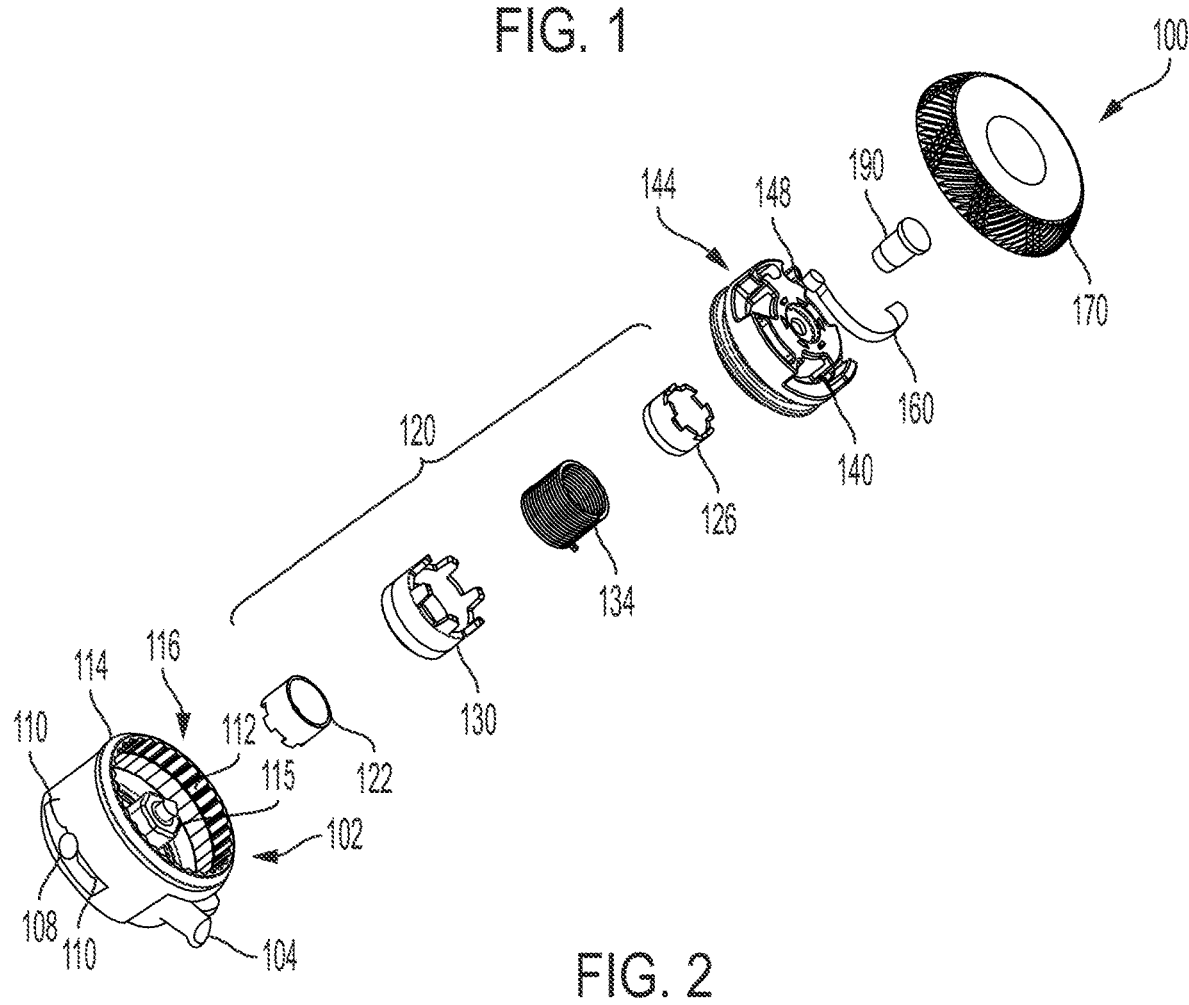
FIGS. 2-3 illustrate exploded perspective views of the reel system of FIG. 1 showing various internal components of the reel system.
Figure 3:
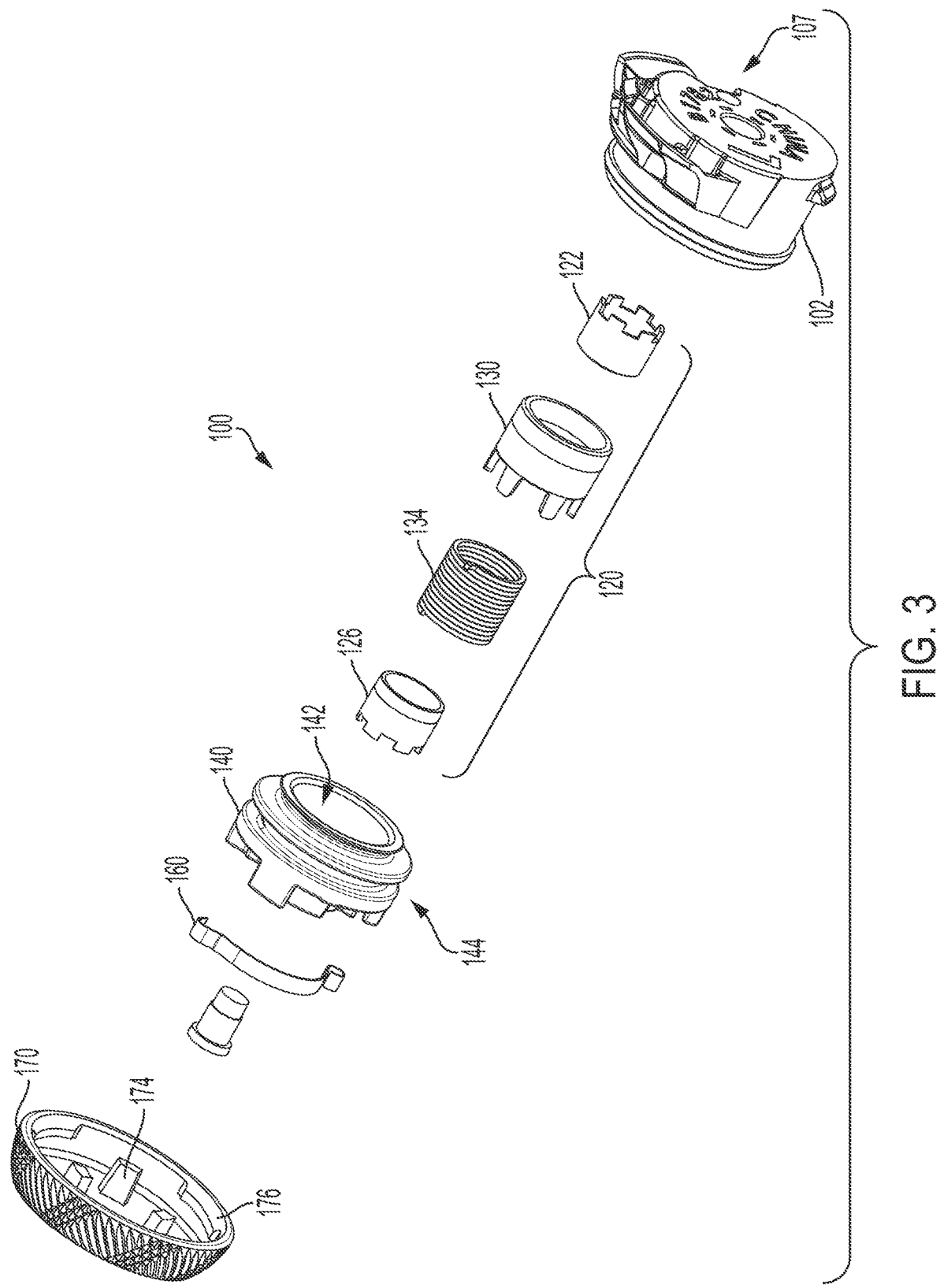

FIGS. 2 and 3 illustrate exploded perspective view of the reel system 100. The internal components of the reel system 100 are visible in FIGS. 2 and 3. The term "internal components" implies the components of the system that are disposed within an interior region 116 of the housing 102 and axially below the knob 170 so that in the assembled view, the internal components are not visible. The internal components include a spool 140, a friction based load holding mechanism 120, an audible feedback assembly 160, and a stop cord or mechanism 230 (see FIG. 20). Each of these components is described in greater detail in relation to FIGS. 2-20, which provide detailed perspective views of the various components.

Figure 9:
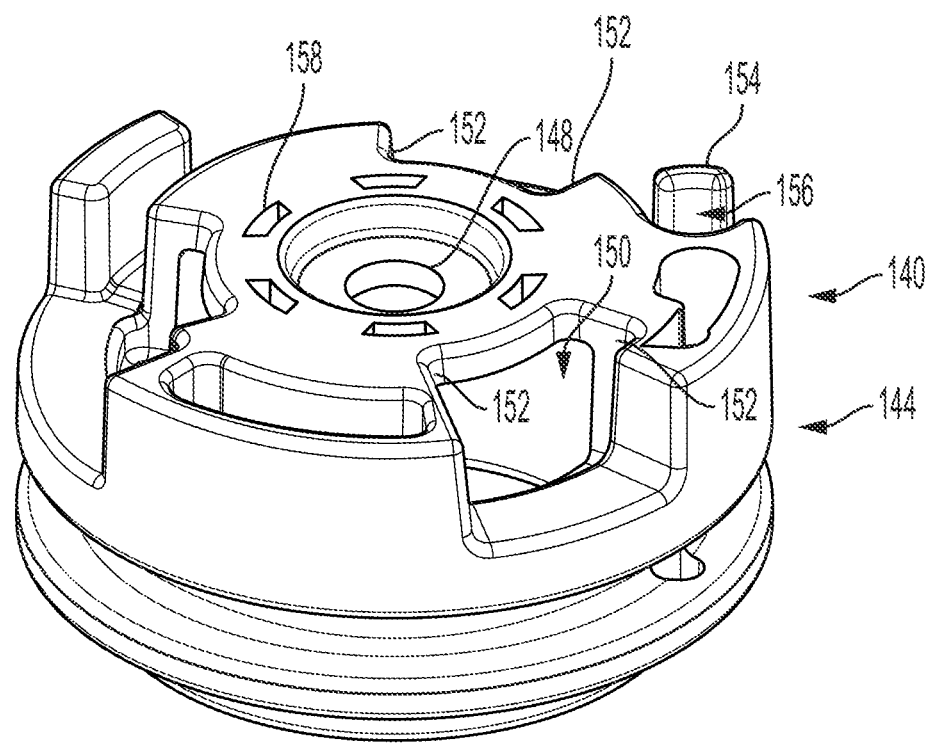
FIG. 9 illustrates an embodiment of a spool that may be employed in the reel system of FIG. 1.

The spool 140 is rotatably positioned within the interior region 116 of the housing 102. A detailed perspective view of the spool 140 is illustrated in FIG. 9. The spool 140 is configured to rotate around a cylindrical coupling post 190 that attaches to a central boss 115 of the housing 102. The cylindrical coupling post 190 is inserted through a central aperture 148 of the spool 140 and attaches to the central boss 115 of the housing 102 by inserting or press fitting a distal end of the cylindrical coupling post 190 within an aperture of the housing's central boss 115 (see FIG. 16). FIG. 16 illustrates the cylindrical coupling post 190 press fit or inserted within the aperture of the central boss 115. The cylindrical coupling post 190 may be secured to the central boss 115 via an interference fit, adhesive bonding, welding (RF, sonic, etc.), and the like. The spool's aperture 148 is sufficiently large so as to minimize frictional forces between the spool 140 and cylindrical coupling post 190 and thereby enable the spool 140 to freely rotate about the cylindrical coupling post 190 within the interior region 116 of the housing 102.

The spool's aperture 148 is centrally positioned within a recessed portion of the upper surface of the spool 140. The recessed portion of the upper surface of the spool 140 is shaped and sized to accommodate a cap of the cylindrical coupling post 190. When the cap of the cylindrical coupling post 190 is positioned within the recessed portion of the spool 140, an upper surface of the cap may align with the upper surface of the spool 140.

The spool 140 includes a lace take up region, such as an annular channel 144, around which the tension member (not shown) is wound and unwound in order to tension and loosen the tension member. The spool 140 is operationally coupled with the knob 170 so that rotation of the knob 170 in a tightening direction (e.g., clockwise) and a loosening direction (e.g., counter-clockwise) effects a corresponding rotation of the spool 140 within the interior region 116 of the housing 102. The knob 170 includes one or more drive components or tabs 174 that are positioned within a window 150 of the spool 140. In the illustrated embodiment, the reel system 100 includes three drive tabs 174 and three windows 150, although more or fewer of these components may be employed as desired.

Figure 12:
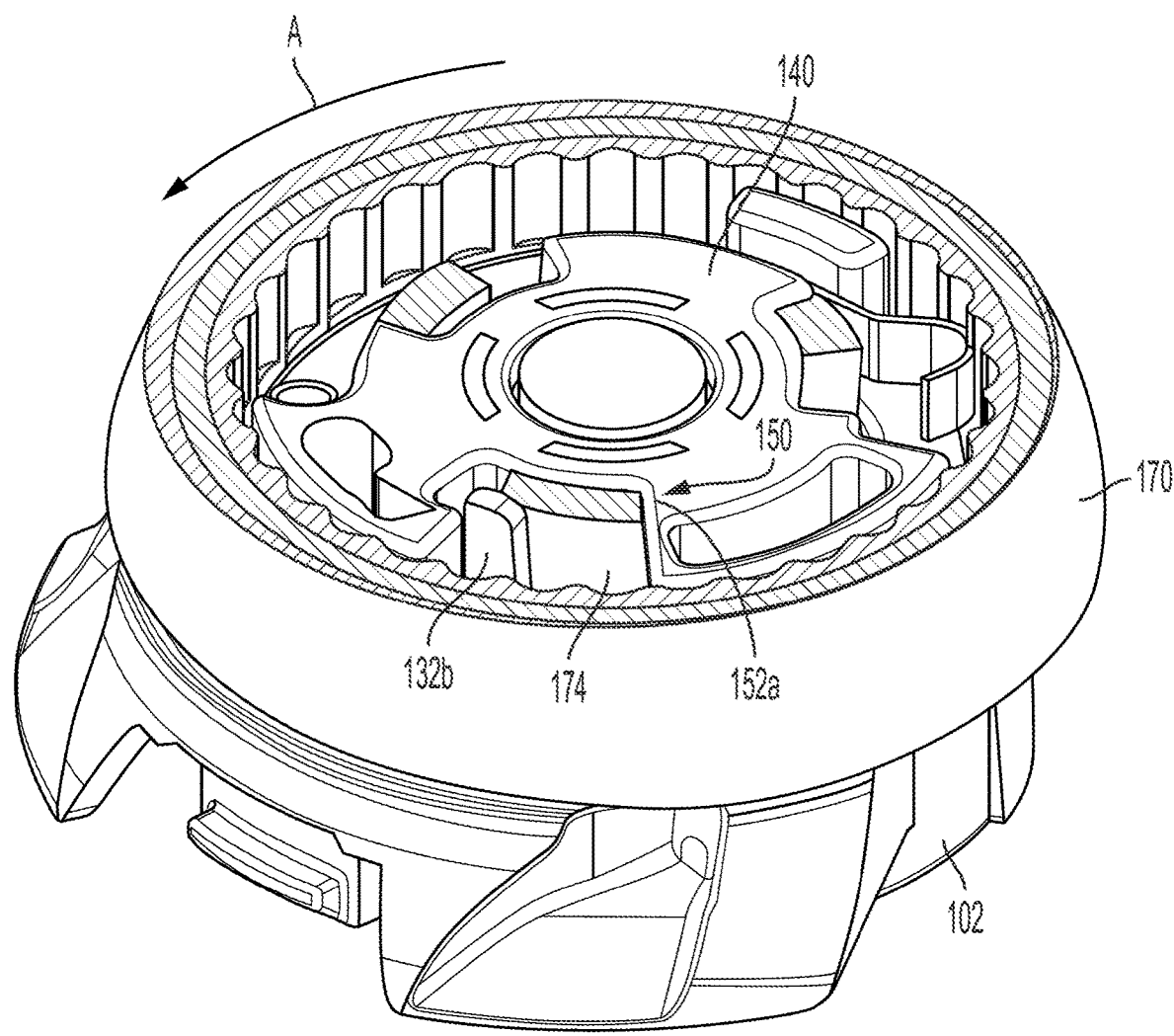
FIG. 12 illustrates a knob member and housing of the reel system of FIG. 1 in which the knob member is rotated in a tightening direction in relation to the housing.
Figure 13:
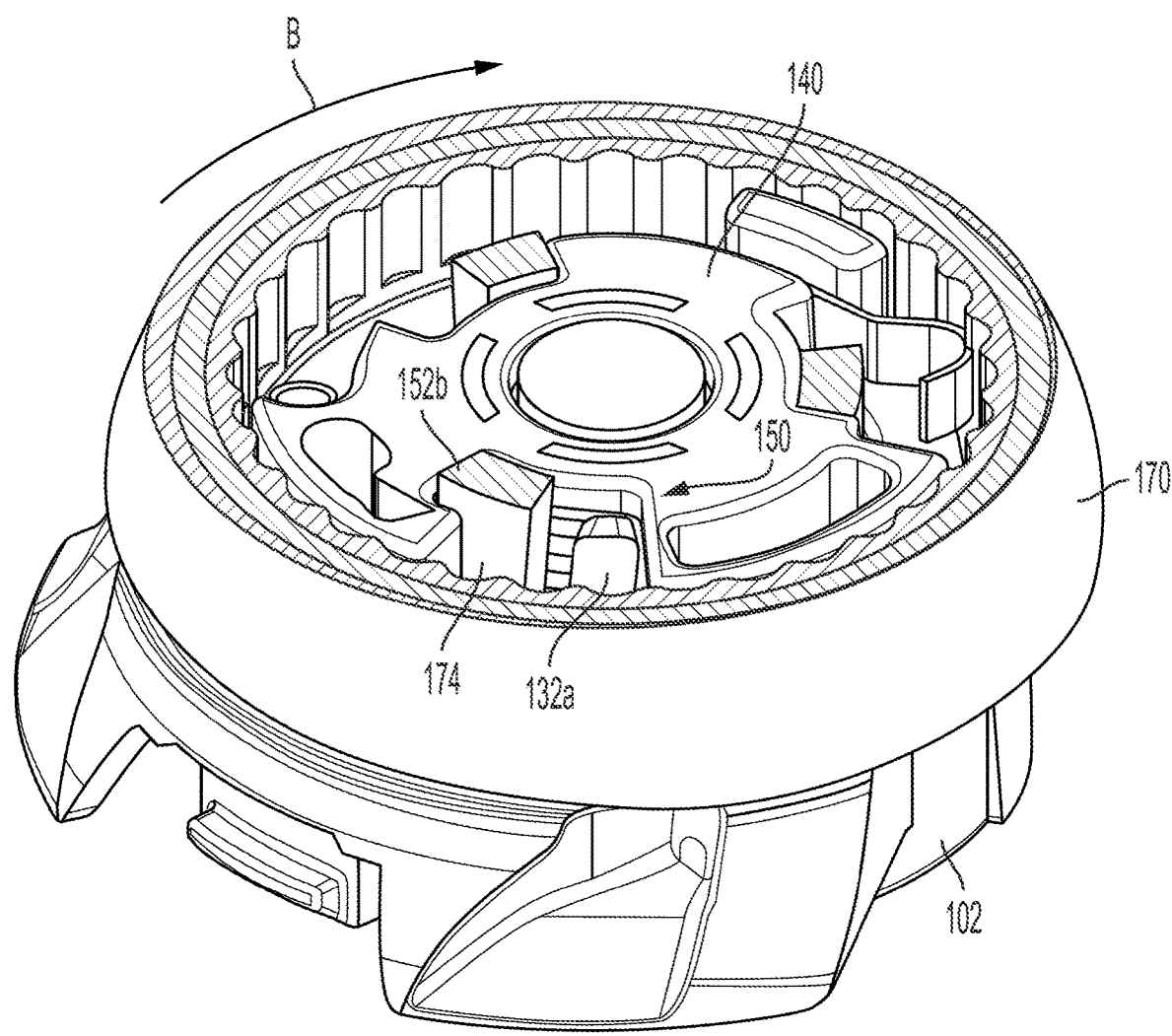
FIG. 13 illustrates the knob member and housing in which the knob member is rotated in a loosening direction in relation to the housing.

The drive tabs 174 are sized smaller than the windows 150 so that the drive tabs 174 are rotatable by some amount within the windows 150 between opposing inner sides or edges 152 of the window 150. The relative rotation of the drive tabs 174 within the windows 150 allows the knob 170 to be rotated about the housing 102 by some amount without effecting a tightening or loosening of the tension member. The smaller sized drive tabs 174 facilitate in releasing the friction based load holding mechanism 120 as described herein. FIGS. 12 and 13 illustrate the drive tabs 174 rotating between the opposing sides 152 of the windows 150 and being used in a manner that enables tensioning and loosening of the tension member by causing the spool 140 to rotate within the interior region 116 of the housing 102.

Figure 10:
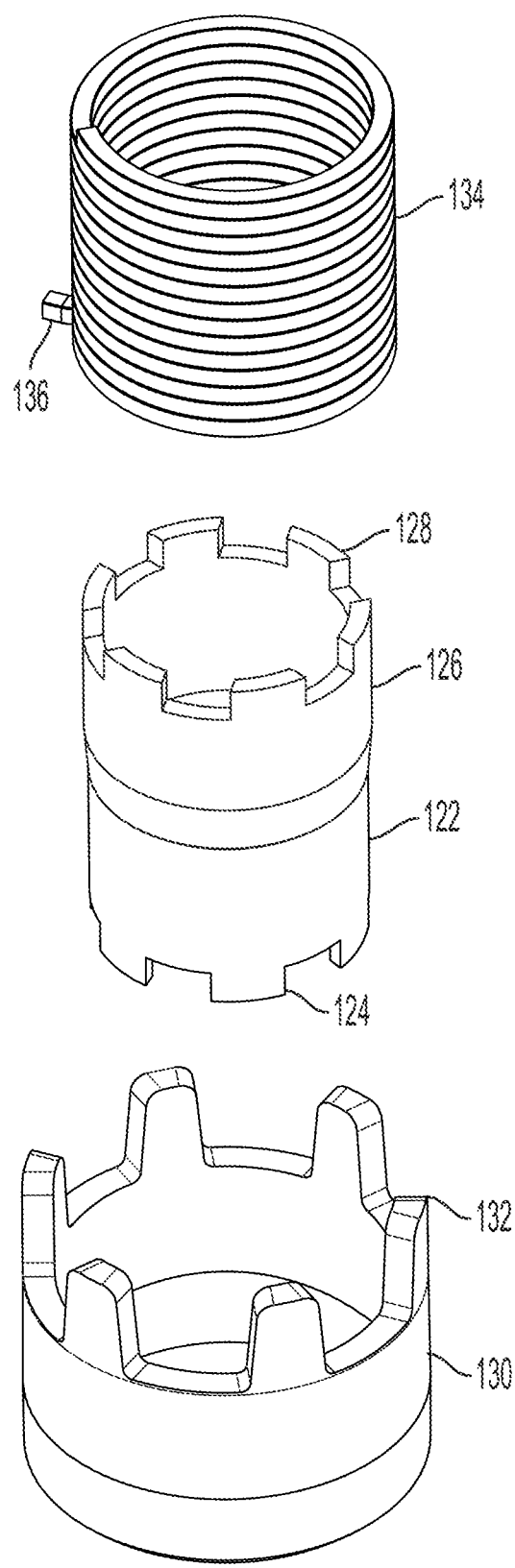
FIG. 10 illustrates an exploded perspective view of a release hub and the upper hub, the lower hub, and the coil spring of FIGS. 6-8.

The bottom or rear surface of the spool 140 includes a large cylindrical opening or channel 142 within which the friction based load holding mechanism 120 is positioned. As illustrated in FIG. 10, the friction based load holding mechanism 120 includes an upper hub 126, a lower hub 122, a coil spring 134, and a release sleeve 134, all or most of which are coaxially aligned and positioned within the opening or channel 142 of the spool 140. The upper hub 126, lower hub 122, and release sleeve 130 all include axially extending teeth. Specifically, the upper hub 126 includes axially extending teeth 128, the lower hub includes axially extending teeth 124, and the release sleeve 130 includes axially extending teeth 132. The axially extending teeth, 128 and 124, of the upper hub 126 and lower hub 122 are oriented so that the teeth extend in opposing directions. The release sleeve 130 is oriented so that its axially extending teeth 132 extend in the same direction as the axially extending teeth 128 of the upper hub 126.

The upper hub 126 is positioned within the cylindrical opening 142 of the spool 140 so that its axially extending teeth 128 are inserted within corresponding apertures 158 of the spool 140, which locks or fixedly secures the upper hub 126 to the spool 140. Fixedly securing the upper hub 126 to the spool 140 means that the upper hub 126 does not translate or rotate relative to the spool 140. Rather, rotational motion or movement of the spool 140 causes a corresponding rotational motion or movement of the upper hub 126 since the two components are fixedly secured together. The lower hub 122 is similarly positioned within the interior region 116 of the housing 102 so that its axial extending teeth 124 are inserted within corresponding apertures 107 of the housing 102, which locks or fixedly secures the lower hub 122 to the housing 102. When coupled with the base member 220, the housing 102 is fixed in position relative to the base member 220. Since the lower hub 122 is locked or fixedly secured to the housing 102, the lower hub 122 is fixed in position relative to the base member and housing and thus, the lower hub 122 is not rotatable or translatable relative to the reel system 100.

The coil spring 134 is positioned over the upper hub 126 and the lower hub 122. The release sleeve 130 is in turn positioned over the coil spring 134 so that the coil spring 134, the upper hub 126, and the lower hub 112 are positioned within the cylindrically interior region of the release sleeve 130. The coil spring 134 surrounds the upper hub 126 and the lower hub 122 in a manner that allows the coil spring 134 to constrict about the outer surfaces of these hubs, 126 and 122. Specifically, the coil spring 134 has an inner diameter that is approximately the same as, or slightly smaller, than an outer diameter of the upper hub 126 and the lower hub 122. The coil spring 134 frictionally engages with the upper hub 126 and the lower hub 122 by constricting about the outer surface of said hubs, 122 and 126. The frictional engagement of the coil spring 134 and the upper and lower hubs, 126 and 122, provides the load holding property or function of the friction based load holding mechanism 120. Specifically, the constriction of the coil spring 134 about the upper hub 126 and the lower hub 122 locks or secures the upper hub 126 and lower hub 122 in relation to one another by preventing the upper hub 126 from rotating about or relative to the lower hub 122. Locking the upper hub 126 and the lower hub 122 together in this manner locks the spool 140 in position relative to the housing 102 since the spool 140 is fixedly secured to the upper hub 126. This prevents the spool 140 from spinning or rotating within the interior region 116 of the housing 102, which maintains a tension that exists in the tension member.

The coil spring 134 is designed so that when the knob 170 is rotated in the tightening direction (e.g., Arrow A in FIG. 12), the coil spring 134 is able to rotate about the lower hub 122, which is fixed in positon about the housing 102. The coil spring 134 typically stays fixed in position about the upper hub 126 and rotates in the tightening direction along with the upper hub 126, the release sleeve 130, the spool 140, and the knob 170. Maintaining a proper alignment of the upper hub 126, the coil spring 134, and the release sleeve 130 is important in delivering a consistent and repeatable tensioning and loosening feel and performance of the reel system 100 as described herein. Rotation of these components in the tightening direction causes the tension member to be wound about the annular channel 144 of the spool 140, which increases the tension in the tension member. When rotation of the knob 170 in the tightening direction ceases, the coil spring 134 constricts about the upper and lower hubs, 126 and 122, thereby locking or securing these components together and preventing rotation of the spool 140 and other components in the loosening direction (e.g., Arrow B of FIG. 13). The tension in the tension member typically biases the spool 140 toward rotation in the loosening direction, which increases the frictional engagement of the coil spring 134 and upper and lower hubs, 126 and 122. The increased frictional engagement of these components further locks, or more fixedly secures, the upper and lower hubs, 126 and 122, together.

The release sleeve 130 is used to adjust the frictional engagement of the coil spring 134 about the upper and lower hubs, 126 and 122, in order to allow the hubs, 126 and 122, to rotate relative to one another and thereby allow the spool 140 to spin within the interior region 116 of the housing 102. Specifically, the release sleeve 130 is operationally coupled with the knob 170 so that rotation of the knob 170 in the loosening direction causes a lower portion of the release sleeve 130 to rotate in the loosening direction. As illustrated in FIG. 13, as the knob 170 is rotated in the loosening direction, the drive tabs 174 of the knob 170 engage the axially extending teeth 132 of the release sleeve 130, which causes the release sleeve 130 to rotate in the loosening direction.

Figure 11:
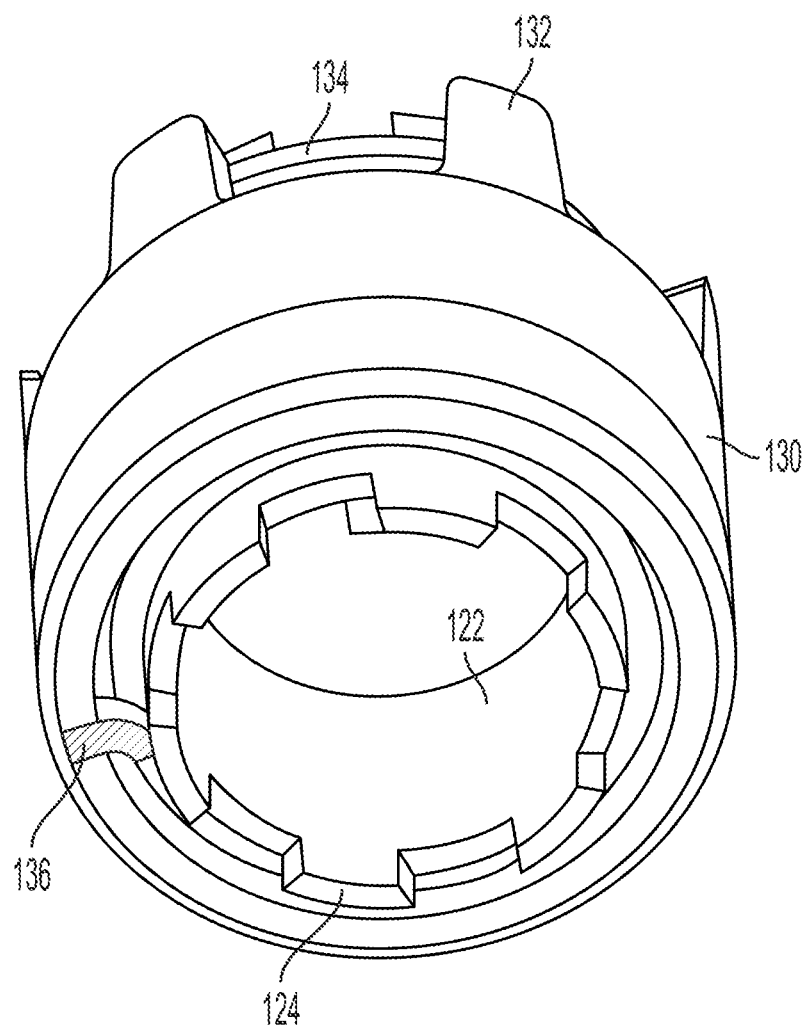
FIG. 11 illustrates an assembled view of the release hub, the upper hub, the lower hub, and the coil spring of FIG. 10.

As illustrated in FIG. 11, an opposite end of the release sleeve 130 is attached to a radially extending tang 136 of the coil spring 134 so that rotation of the release sleeve 130 in the loosening direction presses on the tang 136 which causes the coil spring 134 to open slightly. Specifically, as the release sleeve 130 rotates in the loosening direction, the tang 136 is pressed and rotated in the loosening direction, which causes the lower coil portions of the coil spring 134 to radially open or widen, thereby reducing the frictional engagement of the lower coil portions and the lower hub 122. The reduced frictional engagement of the coil spring 134 and lower hub 122 allows the lower coil portions of the coil spring 134 to rotate about the lower hub 122 in the loosening direction.

The upper portions of the coil spring 134 remain fixed in position about the upper hub 126 so that the upper portions of the coil spring 134 do not rotate about, or relative to, the upper hub 126. Since the lower portions of the coil spring 134 are rotatable about the lower hub 122 via the release sleeve 130, the upper hub 126 and coil spring 134 may be rotated in the loosening direction. In this manner the release sleeve 130 enables the upper hub 126 to be unlocked or uncoupled from the lower hub 122, which allows the upper hub 126 and coil spring 134 to be rotated in the loosening direction in response to rotation of the knob 170 in the loosening direction. Since the upper hub 126 is attached to the spool 140, uncoupling the upper and lower hubs, 126 and 122, allows the spool 140 to be rotated in the loosening direction in response to rotation of the knob 170 in the loosening direction, which unwinds the tension member from the annular channel 144 and thereby reduces tension in the tension member. When rotation of the knob 170 in the loosening direction ceases, the lower portion of the coil spring 134 constricts about the lower hub 122, which locks or couples the upper and lower hubs, 126 and 122, and thereby prevents further rotation of the upper hub 126, the coil spring 134, and the spool 140 in the loosening direction.

The release sleeve 130 is sized radially larger than the coil spring 134 to ensure that the release sleeve 130 does not frictionally engage with, or minimally engages with, the coil spring 134, which engagement may impede rotation of the release sleeve 130 relative to the coil spring 134.

As briefly described above, it is desirable to maintain an orientation of the upper hub 126, the coil spring 134, the release sleeve 130, and the spool 140. A proper orientation of these components is important to ensure that rotation of the knob 170 in the loosening direction causes the release sleeve 130 to engage the tang 136 in a consistent and repeatable manner, which ensures that the tightening and loosening of the tension member remains relatively constant. As illustrated in FIGS. 12 and 13, the axially extending teeth 132 and the drive tabs 174 are positioned within the windows 150 of the spool 140. In order to achieve a repeatable and consistent engagement of the tang 136, it is important to maintain the orientation or relative positions of the axially extending teeth 132 and the drive tabs 174 within the window 150. Otherwise, the drive tabs 174 will not properly engage the axially extending teeth 132 of the release sleeve 130 to cause the release sleeve 130 to rotate and open the lower coil portions of the coil spring 134 as described above.

To maintain the orientation of these components, it is important that the upper coil portions of the coil spring 134 remain fixed about the upper hub 126. Specifically, it is important that the coil spring 134 does not rotate relative to the upper hub 126, but rather only rotates relative to or about the lower hub 122. To ensure that the coil spring 134 rotates about the lower hub 122 only and remains fixed or secured to the upper hub 126, one or more of the following upper and lower hub configurations may be employed: the upper hub 126 may have a slightly larger diameter than the lower hub 122, the upper hub 126 may be made of a material having a greater coefficient of friction than the lower hub 122, the lower hub 122 may have a surface finish that substantially reduces the frictional coefficient in comparison with the upper hub 126. Any combination of these options may be employed to ensure that the coil spring 134 only rotates about the lower hub 122.

Figure 6:
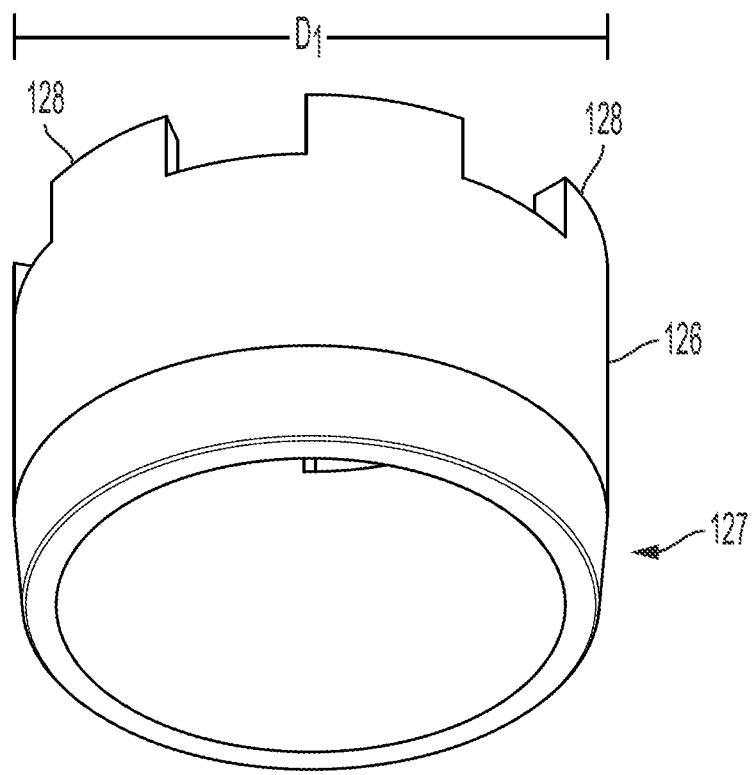
FIGS. 6-7 illustrate an upper hub and a lower hub that may be employed in the reel system of FIG. 1.
Figure 7:
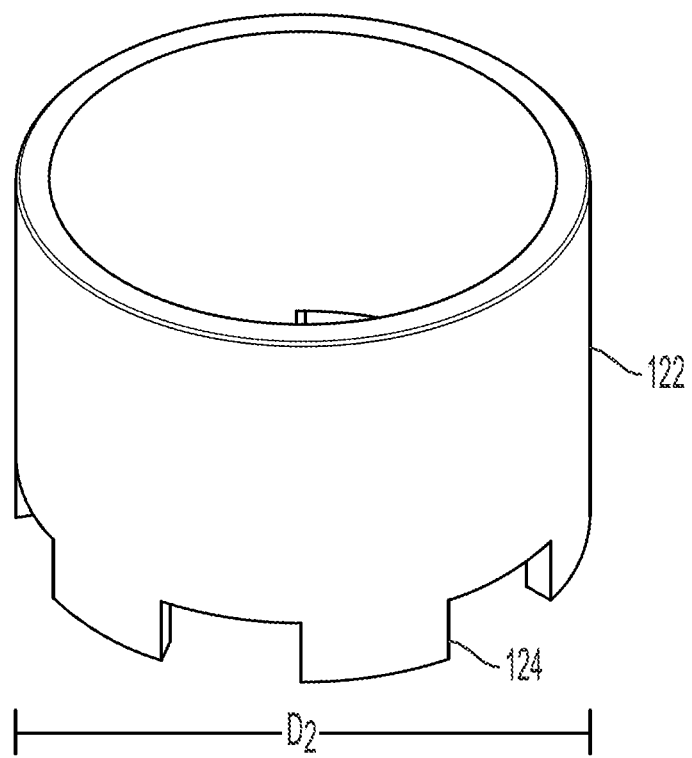
Figure 8:
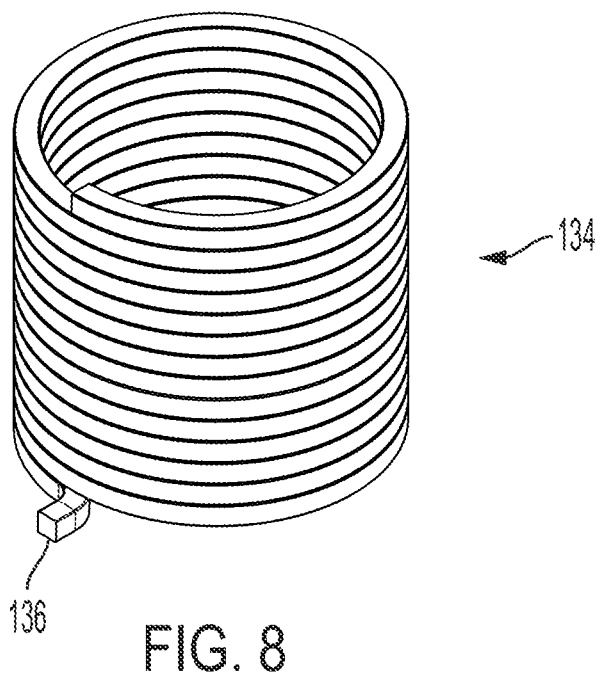
FIG. 8 illustrate a coil spring that may be employed with the upper hub and the lower hub of FIGS. 6-7.

For example, as illustrated in FIGS. 6 and 7, the upper hub 126 may have a diameter $D_1$ that is larger than a diameter $D_2$ of the lower hub 122. The larger diameter $D_1$ of the upper hub 126 ensures that the coil spring 134 constricts about and is more frictionally engaged with the upper hub 126 than the lower hub 122. In some embodiments, the difference in diameter between the upper and lower hubs, 126 and 122, is approximately 2 mm. The 2 mm diameter difference is sufficient to ensure that the coil spring 134 remains frictionally engaged with, and secured to, the upper hub 126 without significantly affecting the load holding power of the system, which may occur when the difference in diameter between the upper hub 126 and the lower hub 122 is too substantial. If the difference in diameter between the upper hub 126 and the lower hub 122 is too great, the coil spring 134 may not be able to sufficiently constrict about the lower hub 122 and thus, the coil spring 134 may not be able to lock or secure the upper and lower hubs, 126 and 122, together.

To help ensure that the coil spring 134 is able to properly constrict about the different sized hubs, the upper hub 126 includes a tapered distal end 127, which provides a transition between the larger diameter upper hub 126 and the smaller diameter lower hub 122. The tapered distal end 127 ensures that a rough step or abrupt edge is not formed at an interface between the two hubs, which may negatively affect the holding power of the reel system 100 by limiting the ability of the coil spring 134 to grip and constrict about the outer surface of the lower hub 122. The tapered distal end 127 allows the coil spring 134 to constrict and grip about the outer surface of the lower hub 122 despite the difference in size of the upper and lower hub. In addition, the upper hub 126 may be made of a material having a greater coefficient of friction than the lower hub 122. For example, the upper hub 126 may be made of aluminum while the lower hub 122 is made of brass or bronze. The surface finish of the lower hub 122 may further, or alternatively, reduce the frictional coefficient of the lower hub 122. For example, the lower hub 122 may have a polished surface finish in comparison with the upper hub 126, which may substantially reduce the frictional coefficient of the lower hub 122.

To maintain the orientation of the components, it is also important to ensure a proper alignment of the release sleeve 130 and the coil spring's tang 136. The alignment of the release sleeve 130 and tang 136 is important to ensure that rotation of the release sleeve 130 in the loosening direction immediately engages the tang 136. In some instances, the distal end of the release sleeve 130 may include a notch or slot within which the tang 136 is positioned. In the instant embodiment, however, the tang 136 is inserted directly into the distal end of the release sleeve 130 as shown in FIG. 11. One method of directly inserting the tang 136 into the distal end of the release sleeve 130 is via heat staking the tang 136 into the release sleeve 130. Directly inserting the tang 136 into the release sleeve 130 eliminates or substantially minimizes any issues associated with manufacturing tolerances, which may vary the relative position of the tang 136 about the release sleeve 130 and significantly affect how the coil spring 134 opens in response to counter-rotation of the knob 170 and release sleeve 130.

Since the coil spring 134 is wrapped around the upper and lower hubs multiple times, any variance in the diameter of either hub, 126 and 122, can significantly affect the position of the tang 136 in relation to the release sleeve 130. For example, a change in diameter of either hub results in a change in the position of the tang 136 relative to the release sleeve 130 that can be modeled by the equation $V=N\pi\Delta D$, where V is the variance in the position of the tang 136 about release sleeve 130, N is the number of wrappings of the coil spring 134, and $\Delta D$ is the change in the diameter of either hub. It has been observed that small variations in the diameter of either or both hubs, 126 and 122, can change the position of the tang 136 by up to 1 mm, which can greatly affect how much the coil spring 134 opens or widens in response to counter-rotation of the release sleeve 130. Directly inserting the tang 136 into the distal end of the release sleeve 130, via heat staking or some other method, negates the affects that any variance in the components of the reel system 100 may have. Rather, directly inserting the tang 136 into the release sleeve 130 ensures a proper and precise alignment regardless of any variance experienced in the system. Eliminating or reducing the variance in the positioning of the tang 136 about the release sleeve 130 typically results in a more consistent and repeatable system performance and feel in tensioning and loosening the tension member.

In some embodiments, the coil spring 134 may be wrapped about the upper and lower hubs, 126 and 122, about 7 times.

FIGS. 12 and 13 illustrate the interaction of the knob 170, the spool 140, and the release sleeve 130 in adjusting the tension of a tension member. FIG. 12 illustrates these components being used to increase the tension of the tension member by winding the tension member around the spool's annular channel 144 while FIG. 13 illustrates these components being used to reduce the tension of the tension member by unwinding the tension member from around the spool's annular channel 144. In the figures, the upper surface of the knob 170 is removed so that the drive tabs 174 of the knob 170, the axially extending teeth 132 of the release sleeve 130, the upper surface of the spool 140, and the spool's windows 150 are visible. As shown in FIG. 12, rotation of the knob 170 in the tightening direction, which is represented by Arrow A, causes the drive tab 174 to contact a first tooth 132a of the release sleeve 130 and a front edge 152a of the spool's window 150 (the first tooth 132a is shown exposed in FIG. 13). Contact between the drive tab 174 and the first tooth 132a causes the release sleeve 130 to rotate relative to the spool 130, which causes the first tooth 132a to rotate out of the window 150 and under the upper surface of the spool 140. Rotation of the release sleeve 130 in this manner causes a second tooth 132b to rotate into the window 150 on an opposite side of the drive tab 174 as illustrated in FIG. 12.

Contact between the drive tab 174 and the front edge 152a of the spool's window 150 transfers rotational forces between the knob 170 and the spool 140. Thus, rotation of the knob 170 in the tightening direction causes the spool to likewise rotate in the tightening direction, which causes the tension member to be wound about the spool's annular channel 144. As illustrated, the instant embodiment includes three drive tabs 174, windows 150, and first teeth 132a, although more or fewer of these components may be employed. In some embodiments, the release sleeve 130 does not include the first tooth 132a and instead rotational forces are transferred to the release sleeve 130 via the coil spring 134 and tang 136.

As shown in FIG. 13, rotation of the knob 170 in a counter direction (i.e., the loosening direction), which is illustrated by Arrow B, causes the drive tab 174 to counter-rotate, or rotate in an opposite direction, within the window 150. This counter rotation of the drive tab 174 causes the drive tab to contact the second tooth 132b and rotate the second tooth 132b and release sleeve 130 in the loosening direction, which causes the release sleeve 130 to rotate the coil spring's tang 136 and open or widen the diameter of the coil spring 134 as described herein. Rotation of the drive tab 174 pushes the second tooth 132b out of the window 150 and under the upper surface of the spool 140 until drive tab 174 contacts a second edge 152b of the window. The first tooth 132a is simultaneously rotated within the window as illustrated. In this manner the knob 170 is rotatable in the loosening direction to engage the release sleeve 130 and thereby reduce the frictional engagement of the coil spring 134 about the lower hub 122, which allows the spool 140, the upper hub 126, and the coil spring 134 to rotate in the loosening direction and thereby reduce the tension in the tension member by unwinding the tension member from the spool's annular channel 144. The tension in the tension member, and/or the drive tab 174 pressing on the second edge 152b, may cause the spool 140 to rotate in the loosening direction.

Since the drive tab 174 is rotatable within the window 150 between the first edge 152a and the second edge 152g, the knob 170 will rotate by some amount relative to the spool 140 before engaging with the spool 140 and causing the spool 140 to rotate in the tightening or loosening direction. In some embodiments the knob 170 may rotate between 3 and 20 degrees relative to the spool 140 before engaging the spool, although a rotation of between 5 and 10 degrees is more common. The relative rotation of the knob 170 about the spool 140 is important to ensure that the drive tab 174 contacts the second tooth 132b before contacting the second edge 152b. This allows the release sleeve 130 to rotate relative to the spool 140 and to rotated relative to the upper and lower hubs, 126 and 122, which opens the coil spring 134 and reduces the frictional engagement of the coil spring 134 and lower hub 122 as previously described.

If the drive tab 174 simultaneously, or nearly simultaneously, contacts the second tooth 132b and the second edge 152b, the coil spring 134 may not open sufficiently and will remain frictionally engaged with the lower hub 122. This frictional engagement of the coil spring 134 and lower hub 122 may require the user to exert substantial force to loosen the tension member and/or may provide a feeling that the system is locked, jammed, or otherwise faulty. Accordingly, maintaining a proper orientation of the release sleeve's teeth, 132a and 132b, in relation to the window 150 and drive tabs 174 is highly desired in order to provide a more consistent and comfortable user experience. The above described approach of fixing the coil spring 134 to the upper hub 126 and directly inserting the tang 136 into the release sleeve 130 help ensure that the proper orientation of the upper hub 126, the coil spring 134, the release sleeve 130, and the spool 140 is maintained, which provides a more uniform and consistent feel and operation of the reel system 100.

Figure 30:
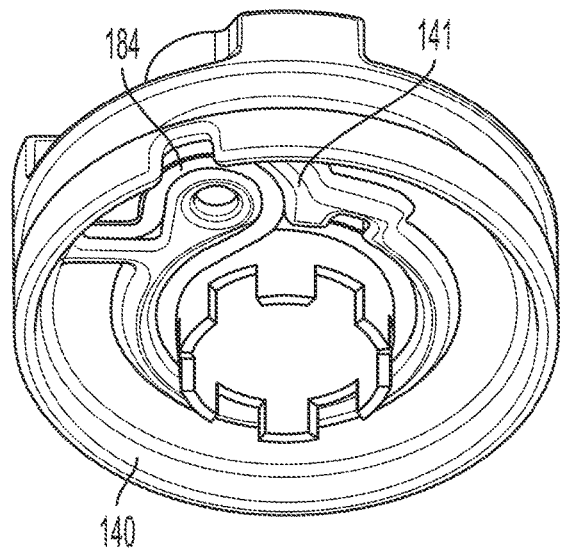

Referring briefly to FIGS. 26-30, illustrated is an alternative embodiment of a friction based load holding mechanism that includes a single hub 180 that frictionally engages with a coil spring 182. The hub 180 and coil spring 182 are configured to be coaxially aligned and positioned within the opening or channel 142 of the spool 140. The hub 180 includes axially extending teeth 124 that fixedly secures the hub 180 to the housing 102. The coil spring 182 includes a U-shaped tang 184 that is configured to couple with a spool 140 by being positioned within a channel 141 of a bottom end of the spool 140 as illustrated in FIG. 30. The U-shaped tang 184 eliminates the need for the upper end of the hub 180 to include axially extending teeth that engage with the spool 140, which design may be employed in the upper hub 126 described herein. The tang 184 may also have a shape other than the U-shape illustrated in FIGS. 26-30. The spool 140 is fixedly secured to the housing 102 via engagement of the axially extending teeth 124 of the hub 180 and the tang 184 of the hub 180.

Figure 27:
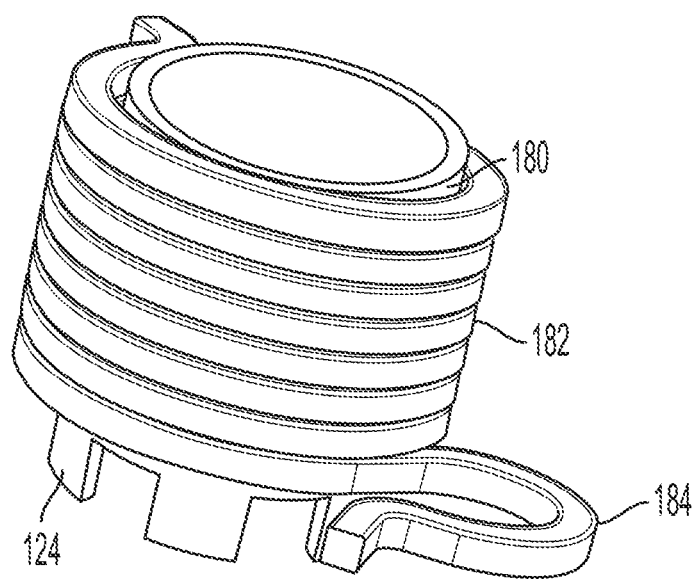
Figure 28:
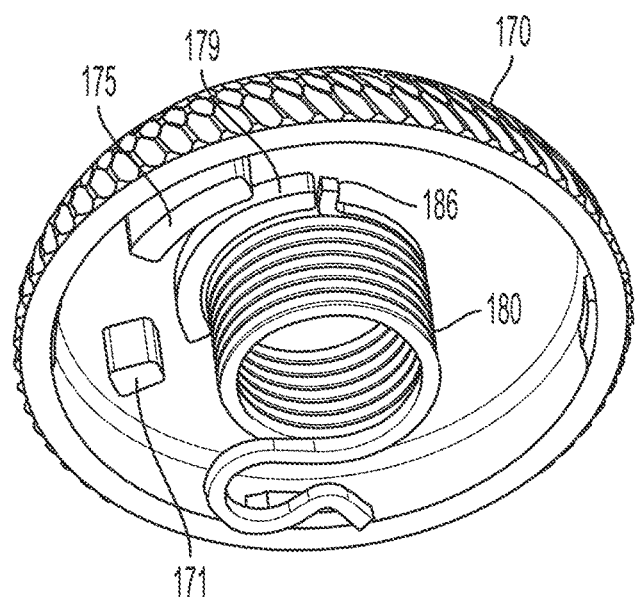
Figure 29:
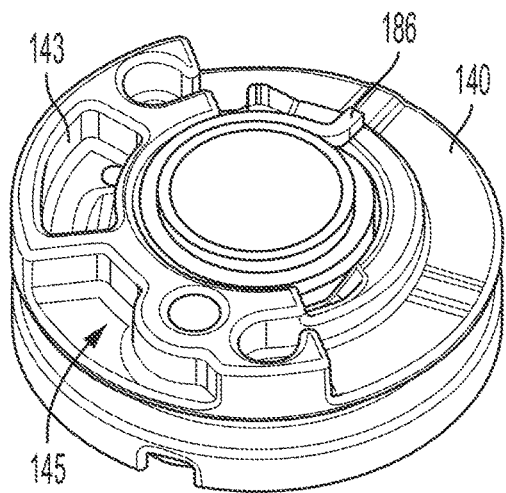

FIG. 27 illustrates the coil spring 182 wound about an exterior surface of the single hub 180. As described herein, the coil spring 182 is designed to constrict about the hub 180 and thereby frictionally engage with the hub 180 to prevent unwanted rotation of the spool 140 within the housing 102. The frictional engagement of the coil spring 182 and the hub 180 provides the load holding property or function of the friction based load holding mechanism. Specifically, the constriction of the coil spring 182 about the hub 180 locks or secures the spring 182 about the hub 180, which locks or secures the spool 140 in position relative to the housing 102 since the spool 140 is secured to the hub 180. Thus, unwanted rotation of the spool 140 within the housing 102 is prevented.

The knob 170, spool 140, and coil spring 182 are designed so that when the knob 170 is rotated in the tightening direction (e.g., Arrow A in FIG. 12), the spool 140 and coil spring 182 are able to rotate about the hub 180, which is fixed in positon about the housing 102. To able rotation of the spool 140 and coil spring 182 about the hub 180, the knob 170 includes axially extending projections, 171 and 175, that are positioned within corresponding recesses, 143 and 145, of the spool 140. The axially extending projections, 171 and 175, contact and engage with the corresponding recesses, 143 and 145, of the spool 140 to transfer rotational forces that are imposed on the knob 170 from the user. The rotational forces 140 cause the spool 140 to rotate about the hub 180. The coil spring 182 is able to rotate about the hub 180 due to the coupling of the U-shaped tang 184 with the spool 140. Specifically, as the spool 140 rotates in the tightening direction, the rotation of the spool 140 transfers a rotational force to the U-shaped tang 184, which widens a diameter of the coil spring 182 and reduces the frictional engagement of the coil spring 184 and hub 180 to the point that rotation of the coil spring 182 about the hub 180 is enabled. Ceasing the rotation of the knob 170 in the tightening direction causes the coil spring 182 to immediately reengage with the hub 180, which locks or secures the spool 140 in position relative to the housing 102.

The knob 170, spool 140, and coil spring 182 are designed so that when the knob 170 is rotated in the loosening direction (e.g., Arrow B in FIG. 13), the spool 140 and coil spring 182 are also able to rotate about the hub 180, which is fixed in positon about the housing 102. The knob includes a release protrusion 179 that is configured to contact and engage with an upper tang 186 of the coil spring 182 when the knob 170 is rotated in the loosening direction. Engagement of the release protrusion 179 and upper tang 186 transfers a rotational force to the upper tang 186, which widens the diameter of the coil spring 182 and reduces the frictional engagement of the coil spring 182 and hub 180 to the point that rotation of the coil spring 182 about the hub 180 is enabled. Since the frictional engagement of the coil spring 182 and hub 180 is reduced, the tension in the tension member, and/or the rotation forces imposed on the knob 170, causes the spool 140 to rotate in the loosening direction. Ceasing the rotation of the knob 170 in the loosening direction causes the coil spring 182 to immediately reengage with the hub 180, which locks or secures the spool 140 in position relative to the housing 102.

A method of assembly an article with a reel based tensioning device may include providing a reel based tensioning device, in which the reel based tensioning device includes a housing, a spool rotatably positioned within the housing, a knob member that is operably coupled with the spool to cause the spool to rotate within the housing, and a load holding mechanism that includes a spring that frictionally engages with a cylindrical member to prevent unwanted rotation of the spool within the housing. The knob member may be operationally coupled with the load holding mechanism so that a first operation of the knob member reduces the frictional engagement of the spring and cylindrical member to allow rotation of the spool within the housing to wind a tension member about the spool and so that a second operation of the knob member also reduces the frictional engagement of the spring and cylindrical member to allow rotation of the spool within the housing to unwind the tension member from about the spool. The method may also include coupling the reel based tensioning device member with the article.

The spring may be a coil spring that is wound about an exterior of a cylindrical hub member, in which the coil spring frictionally engages with the hub member by constricting about an outer surface of the hub member. In some embodiments, the hub member may include an upper hub member that is fixedly secured to the spool and a lower hub member that is fixedly secured to the housing. The upper hub member may have a diameter that is slightly larger than a diameter of the lower hub member and a distal end of the upper hub member that interfaces with the lower hub member may be tapered. Alternatively or additionally, the hub member may be an inner hub member and the reel based tensioning device may also include an outer hub member that is disposed over the inner hub member and that is operationally coupled with the knob member and the spring so that rotation of the knob member in a loosening direction reduces the frictional engagement of the spring and the inner hub member. The outer hub member may be coupled with the knob member so that rotation of the knob member in the loosening direction effects a rotation of the outer hub in the loosening direction. The spring may include a tang that is coupled with the outer hub member so that rotation of the outer hub member in the loosening direction effects a widening of a diameter of the spring, thereby reducing the frictional engagement of the spring and the inner hub member. In other embodiments, the cylindrical member may include a cylindrical channel or recess and the spring may be a coil spring that is biased radially outward into frictional engagement with an interior wall of the cylindrical channel or recess.

Figure 4:
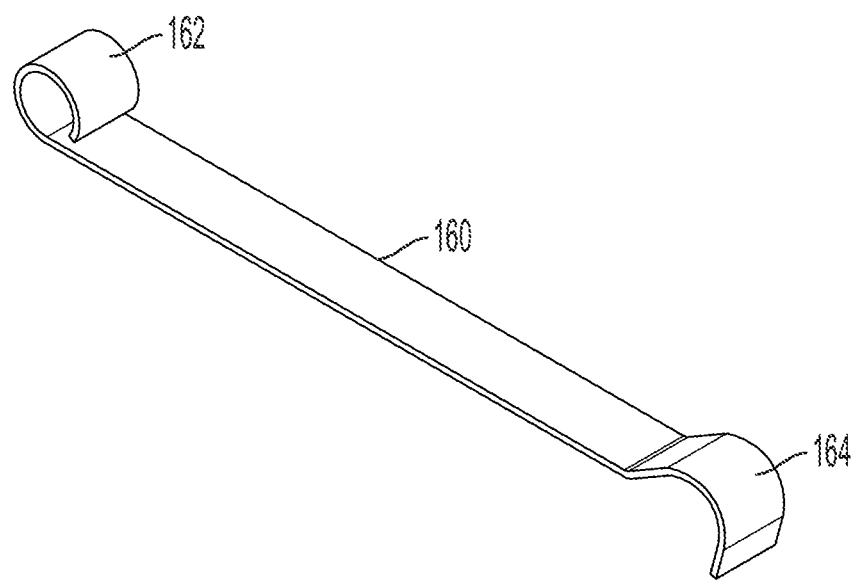
FIG. 4 illustrates a pawl member or beam of an audible component or mechanism.
Figure 14:
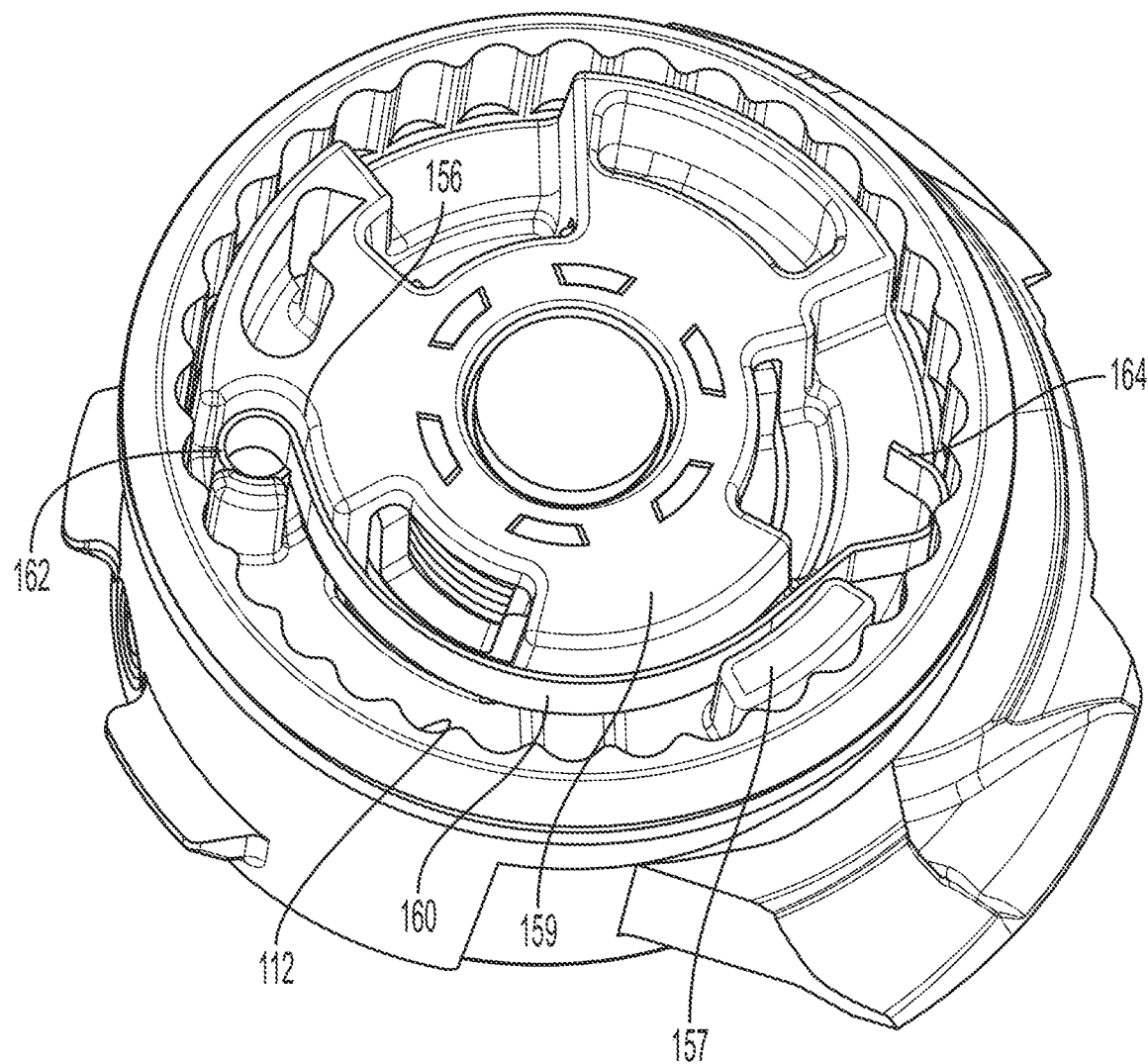
FIG. 14 illustrates a perspective view of an audible component or mechanism of the reel system of FIG. 1 that may be employed to produce an audible noise.

The friction based load holding mechanism 120 is typically a silent mechanism, which means that the friction based load holding mechanism 120 produces essentially no audible sound or minimizes the amount of audible noise that is produced. The description of nondetectable/undetectable audible noise as used herein refers to any noise level below those outlined in MIL-STD-1474D, Req. 2, pgs. 20-32, the entire disclosure of which is incorporated by reference herein. In some instances it may be desirable to provide audible feedback about the use of the reel system 100. To provide the audible feedback, the reel system 100 may include a separate audible mechanism, such as a pawl system that produces an audible click when the reel system 100 is operated. FIG. 14 illustrates an assembly of the components of the system that may be used to produce an audible click and FIG. 4 illustrates a pawl member 160 of the audible mechanism. The pawl member 160 includes an elongate body, a first end 162, and a second end 164. The first end 162 is configured to couple with the upper surface of the spool 140 while the second end 164 is configured to interact with teeth 112 that are positioned on the interior region 116 of the housing 102.

As illustrated in FIG. 14, the first end 162 of the pawl member 160 is positioned within a coupling slot or recess 156 of the spool 140. In the instant embodiment, the first end 162 of the pawl member 160 is bent to form a loop that fits within the slot or recess 156 of the spool 140, although other methods of attaching the first end 162 of the pawl member to the spool may be employed. When positioned within the housing 102, the pawl member 160 flexes and bends between the first end 162 and the second end 164. The elongate body of the pawl member 160 is positioned radially outward of a central portion 159 of the spool 140 and is flexed around the central portion 159. In some embodiments, the pawl member 160 may be positioned radially inward of an outer protrusion 157 of the spool 140. The outer protrusion 157 may hold the pawl member 160 in place during assembly of the reel system 100 and/or affect the flexibility of the pawl member 160 in order to produce a desired audible sound.

The second end 164 of the pawl member 160 contacts the inner surface and teeth 112 of the housing 102. The second end 164 may be shaped so that the second end 164 easily slides about the inner surface of the housing 102 and is deflected into and out of the teeth 112. In one embodiment, the second end 164 of the pawl member has a U-shaped configuration, which allows the second end 164 to easily slide about the inner surface of the housing and minimizes engagement of the second end 164 of the pawl member 102 and the teeth 112 that would impeded or hinder such movement. Unlike conventional pawls, the second end 164 of the pawl member 160 is not designed to restrict or appreciably resist rotation of the spool 140 within the housing 102.

As the spool 140 is rotated in either the tightening or loosening direction within the housing 102, the second end 164 is deflected into and out of adjacent teeth 112 of the housing 102. The second end 164 produces an audible click noise as the second end 164 springs or bounces into engagement with each of the teeth 112 of the housing 102. As the spool 140 is rotated in one direction, the pawl member 160 is tensioned and the second end 164 is pulled into and out of each tooth 112 of the housing 102. As the spool 140 is rotated in the opposite direction, the pawl member 160 is compressed and the second end 164 is pushed into and out of each tooth 112. In this manner, an audible click sensation is produced as the reel system 100 is operated to both tension and loosen the tension member.

The second end 164 of the pawl member 160 may be configured to produce an essentially uniform sound regardless of the direction of rotation of the spool, or may be configured to produce a different sound for when the spool 140 is rotated in the tightening direction versus the loosening direction. For example, the second end 164 may be configured to respond slightly differently when pulled into engagement with each tooth 112 versus when it is pushed into engagement with each tooth, which may produce a different audible sound. The sound may also be adjusted by selecting the thickness of the pawl member 160, the length of the pawl member 160, and/or the number of teeth that are employed in the system. In some embodiments, the spool 140 may include between about 20 and 40 teeth, and more commonly between about 25 and 35 teeth. In a specific embodiment, the spool 140 may include 32 teeth. The reel system 100 could also implement multiple pawl members (e.g., two or more) with each pawl member being employed during the tensioning or loosening of the tension member. In other embodiments, the audible mechanism could include detents that engage to produce an audible sound or a linear pawl beam that interacts with spline teeth.

A method of configuring a reel based tensioning device may include providing a reel based tensioning device, in which the reel based tensioning device includes a housing, a spool that is rotatably positioned within the housing, a knob member that is operably coupled with the spool to cause the spool to rotate in a first direction within the housing to wind a tension member about the spool, and a load holding mechanism that is coupled with the spool and that is configured to allow rotation of the spool in the first direction within the housing and to prevent rotation of the spool in a second direction within the housing to prevent unwinding of the tension member from about the spool. The method may also include coupling an audible component with the reel based tensioning device in which the audible component is configured to produce an audible noise responsive to operation of the knob member to signal an adjustment of the tension member. The method may also include adjusting the audible component to adjust the audible noise that is produced by the audible component.

The load holding mechanism may not produce an audible noise that is detectable by a human ear. The audible component may be configured to produce an audible noise responsive to tensioning of the tension member and to produce an audible noise responsive to loosening of the tension member. The audible noise that is produced responsive to tensioning of the tension member may be different than the audible noise responsive to loosening of the tension member. The audible component may include a pawl member or beam that engages with the housing to produce the audible noise. The pawl member or beam may be incapable of preventing rotation of the spool within the housing when an appreciable rotational force is imposed on the spool via the tension member or knob member. The load holding mechanism of the reel base tensioning device may not include a pawl member or beam.

In some instances, it may be beneficial to form a component of the reel system 100 directly onto a fabric material so that the fabric is integrally formed with or integrated within the component. In some embodiments the fabric material may facilitate in attaching the component with an article, such as attaching the component to a shoe. In a specific embodiment, the component may be formed onto the fabric material via insert molding in which the fabric material is positioned within a mold or die and a polymer material is injected atop or through the fabric material. The component of the reel system may be a first component that includes a top end, a bottom end, and an interior cavity within which a second component of the reel based tensioning system is positionable. A specific example of a first component is a base member or bayonet that is configured to couple with a housing of the reel system. Another example of a first component is a housing that is configured to couple with a spool and other components of the system as described herein. Yet another example of a first component is a guide member that includes an interior cavity that is configured to receive a tension member of the reel system in order to guide the tension member about a path of an article.

When the component is formed onto the fabric material, the fabric material may be positioned near the bottom end of the component and may extend laterally from at least a portion of an outer periphery of the component, and more commonly around the entire periphery of the component. The fabric material may be integrally coupled with the first component by injecting the polymer material (i.e., thermoplastic or thermoset material) of the component through the fabric material so that the polymer material of at least a portion of the component is saturated or impregnated through the fabric material with the polymer material extending axially bellow a bottom surface of the fabric material and axially above a top surface of the fabric material. In some embodiments the polymer material may be saturated or impregnated through the fabric material so that an entire bottom end of the component extends axially bellow the bottom surface of the fabric material and axially above the top surface of the fabric material. In such embodiments, the polymer material of the component's bottom end may form an annular ring on the bottom surface of the fabric material. In other embodiments only a portion of the bottom end may extend axially above and below the fabric material with the remaining portion of the bottom end positioned only on one side of the fabric material.

Figure 15:
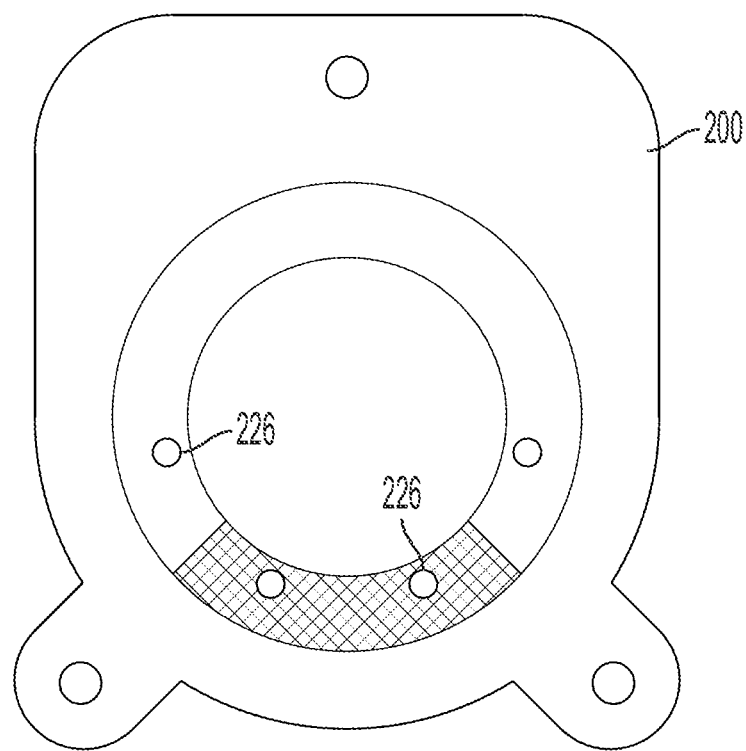
FIGS. 15, 17-19, & 23-25 illustrate various views of a base member, a woven material or fabric, and a coupling of the base member and woven material or fabric.
Figure 18:
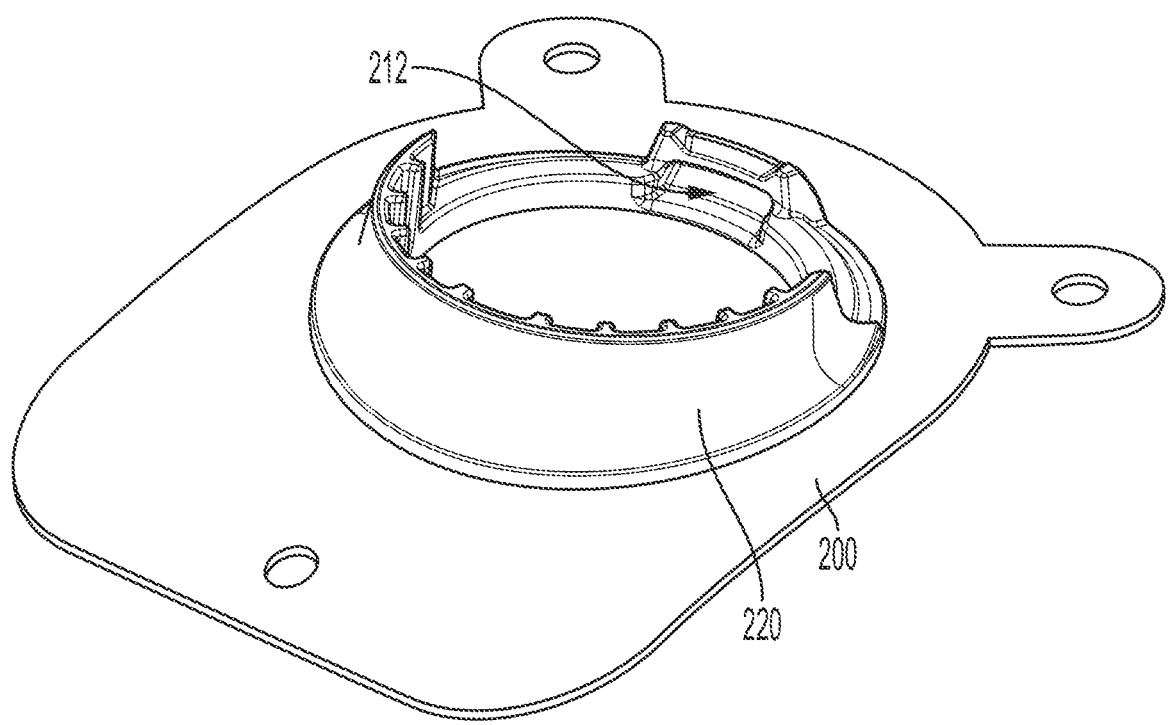
Figure 19:
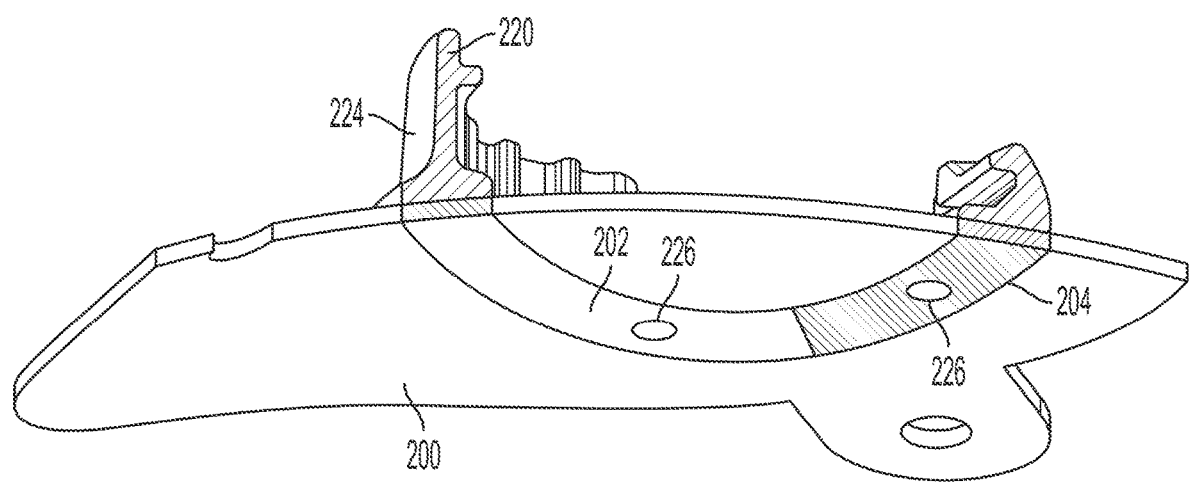
Figure 23:
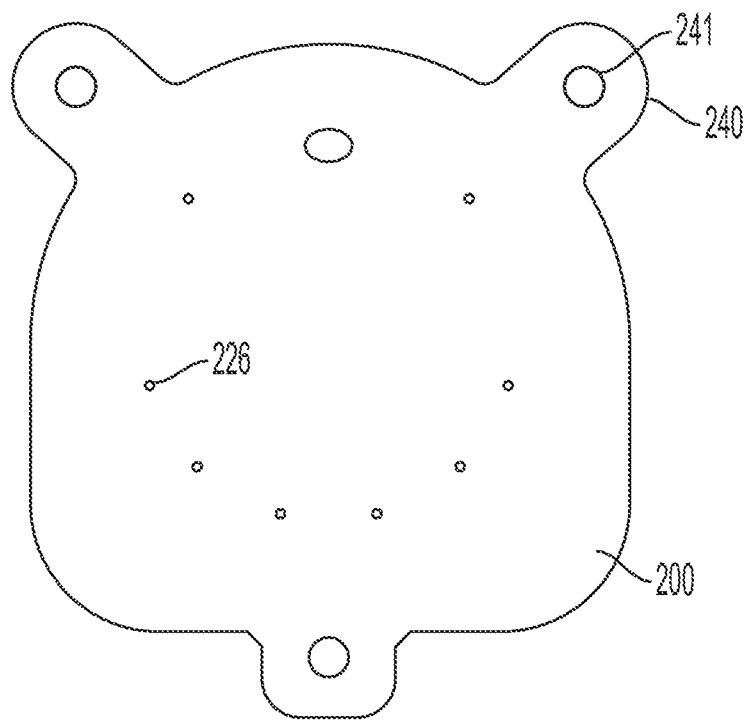
Figure 24:
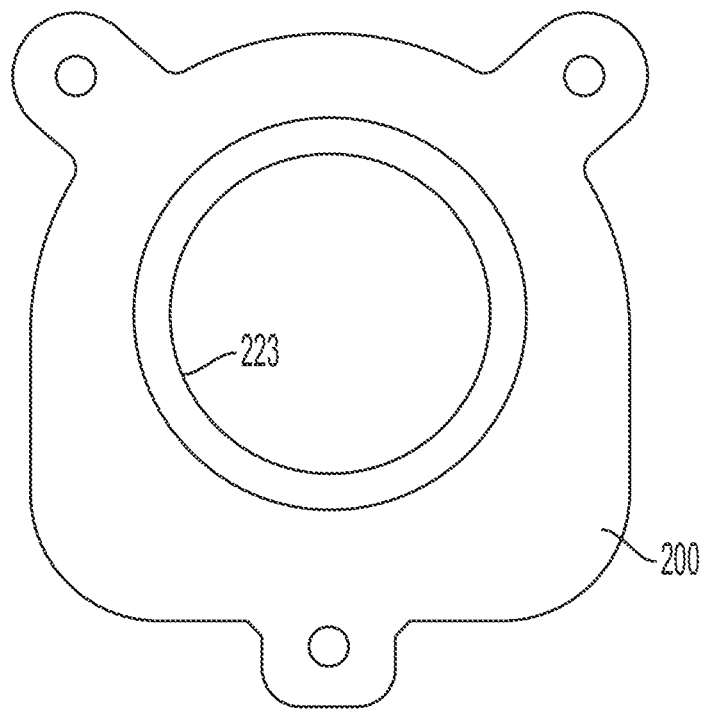

Referring now to FIGS. 15, 17-19, and 23-25 illustrated is the base member 220 attached to a piece of woven material, such as fabric 200. The fabric may be essentially any fabric, such as a polymer based fabric. In a specific embodiment, the fabric may be a 500 denier polyester fabric. FIG. 17 illustrates the base member 220 unattached from the fabric 200 while FIG. 18 illustrates a perspective view of the base member 220 attached to the fabric 200. As illustrated in FIG. 18, the fabric 200 is substantially flush with a bottom surface of the base member 220 after the base member 220 is attached to the fabric 200. The fabric 200 extends laterally from at least a portion of an outer periphery of the base member 220 and more commonly around an entire periphery of the base member 220. FIG. 15 and FIG. 24 illustrate bottom views of the fabric 200 and base member 220 showing alternative attachment configurations of the base member 220 and fabric 200. FIG. 23 illustrates a bottom view of an embodiment of the fabric 200 prior to forming the base member 220 onto the fabric 200. FIG. 19 illustrates a cross sectional view of an embodiment of an attached base member 220 and fabric 200.

In an exemplary embodiment, the base member 220 is directly injected onto the fabric 200. This is achieved by insert molding or injecting the material of the base member 220 through a bottom surface of the fabric 200, which results in a significantly high adhesion strength and prevents or minimizes separation of the base member 220 from the fabric 200. For example, direct injection of the base member's material through the bottom surface of the fabric 200 may enable the materials to experience a 50 Kg force before beginning to separate. The material of the base member 220 is commonly a polymer material (i.e., thermoplastic or thermoset material), which is injected through the fabric 200 so that when the base member 220 is formed, the fabric 200 is disposed within at least a portion of the base member 220 so that the polymer material is disposed on opposite sides of the fabric 200. The positioning of the fabric 200 within the base member 220 is shown in FIGS. 15, 19, and 24.

As illustrated in FIG. 17, the base member 220 may be a component of the system that includes an interior cavity that is configured to receive and releasably couple with a housing 102 as shown in FIG. 16. In other embodiments, the base member may be a housing component, such as the one illustrated in FIG. 16, which may be directly injected onto, and integrally formed with, the fabric 200. In such embodiments, the need for a separate base member 220 and housing 102 may be eliminated and these components may be integrated into a single component that is integrally coupled with the fabric 200. The housing component may include lace ports 104 through which a tension member or lace is disposed.

In some instances, the material of the base member may be injected into the fabric 200 so that the saturation or integration of the material within the fabric 200 is varied. The term saturation or integration of the base member's material within the fabric 200 refers to the amount of the base member's material that remains disposed within the interior of the fabric 200 after the injection process. When the base member's material is highly saturated/integrated within the fabric 200, the injected base member material is essentially positioned on both sides of the fabric 200 and through the interior of the fabric. When the base member's material is less saturated/integrated within the fabric 200, the injected base member material does not fully penetrate through the fabric 200 or is essentially positioned on one side of the fabric 200. The fabric is more readily visible in areas where the base member's material is less saturated/integrated within the fabric 200. In a specific embodiment, the base member's material is glass filled polypropylene and/or co-polyester.

In one embodiment, the saturation/integration of the base member's material may vary from between segments or portions of the base member so that the base member's material is highly saturated/integrated through the fabric 200 in one segment or portion of the base member and less saturated/integrated through the fabric 200 in another segment or portion of the base member. In such an embodiment, the variance of the base member's material within the fabric 200 is illustrated by the cross hatching or shaded areas of FIGS. 15 and 19. The cross hatching or shaded areas represent portions of the fabric 200 where the base member's material is more saturated or integrated into the fabric 200. These areas may appear darker or of a slightly different color due to the base member's material being more concentrated in these areas and more visible from a bottom surface of the fabric 200. The variance of the saturation/integration of the base member's material may be designed to provide a desired property, such as increased bond or adhesion strength between the two materials, increased strength of the base member, etc.

The strength of the bond or adhesion between the fabric 200 and base member 220 may be substantially increased when the base member's material is highly saturated/integrated within the fabric 200. However, the strength of the base member 220 itself may be decreased when the base member's material is highly saturated/integrated within the fabric 200 due to less material being present within the base member. The decreased strength of the base member 220 may negatively affect how the base member 220 interacts with other components of the system, such as the housing 102. For example, a wall 224 that is opposite the front tab 222 may be a thinner section of material in order to reduce the size and/or weight of the base member 220. If the base member 220 is too thin near the wall 224, the wall 224 may crack or break from the pressure or force that is exerted on the wall 224 by the housing 102. As such, it may be desirable to construct the base member 220 and fabric 200 so that the wall 224 remains relatively strong and reinforced while an increased bond/adhesion between these materials is achieved due to saturation of the base member's material within the fabric 200.

In some instances, the base member 220 may experience greater external forces near the front tab 222. The external force may urge or cause the base member 220 to peel away from the fabric 200 and thus, an increased bond/adhesion strength near the front tab 222 may be desired. The wall 224 may be used primarily to couple the base member 220 with the housing 102 and thus, it may be more desirable to reinforce or strength the base member 220 adjacent the wall 224. This increased bond/adhesion strength near the front tab 222 and the increased reinforcement of the base member 220 near the wall 224 may be achieved by increasing the saturation/integration of the base member's material near the front tab 222 while decreasing the saturation/integration of the base member's material near the wall 224 as shown in FIGS. 15 and 19.

In one embodiment, the amount of saturation/integration of the base member's material within the fabric 200 may be controlled based on the arrangement of injection holes 226 that inject the base member's material through the fabric 200. The base member's material may more fully saturate/integrate into the fabric 200 around the injection holes 226 and thus, the injection holes 226 may be positioned adjacent areas of the base member 220 where an increased bond/adhesion strength is desired and may not be positioned in areas where increased component strength is desired. FIGS. 15 and 19 illustrate the injection holes 226 positioned near the front tab 222 where the cross-hatching or shading is illustrated and where increased saturation/integration of base member's material and fabric 200 is typically desired. In this manner, the hole pattern may be engineered to provide a designed combination of desired strength without compromising the integrity of the component.

In another embodiment, the saturation/integration of the base member's material may be relatively uniform relative to the base member so that the base member's material is either highly saturated/integrated through the fabric 200 or slightly saturated/integrated through the fabric 200. FIG. 24 illustrates a bottom view of the fabric 200 that shows a uniform saturate/integration of the polymer material through the fabric. In FIG. 24, the base member's material is highly saturated/integrated through the fabric 200, which results in the fabric 200 being disposed within the polymer material of essentially an entire bottom end of the base member 220. The description of the fabric 200 being disposed within the polymer material of the base member 220 means that the polymer material is disposed or positioned on opposite sides of the fabric 200. Since the base member 220 has an essentially cylindrical configuration as shown in FIG. 17 (i.e., a circular bottom end and hollow interior), the positioning of the polymer material on opposite sides of the fabric 200 results in the formation of an annular ring 223 on a bottom surface of the fabric 200 as illustrated in FIG. 24. When the bottom end of the base member 220 has a different configuration (e.g., planar surface, oval shave, etc.), the shape that is formed on the bottom surface of the fabric 200 would correspond to the shape of the bottom end of the base member 220.

Figure 25:
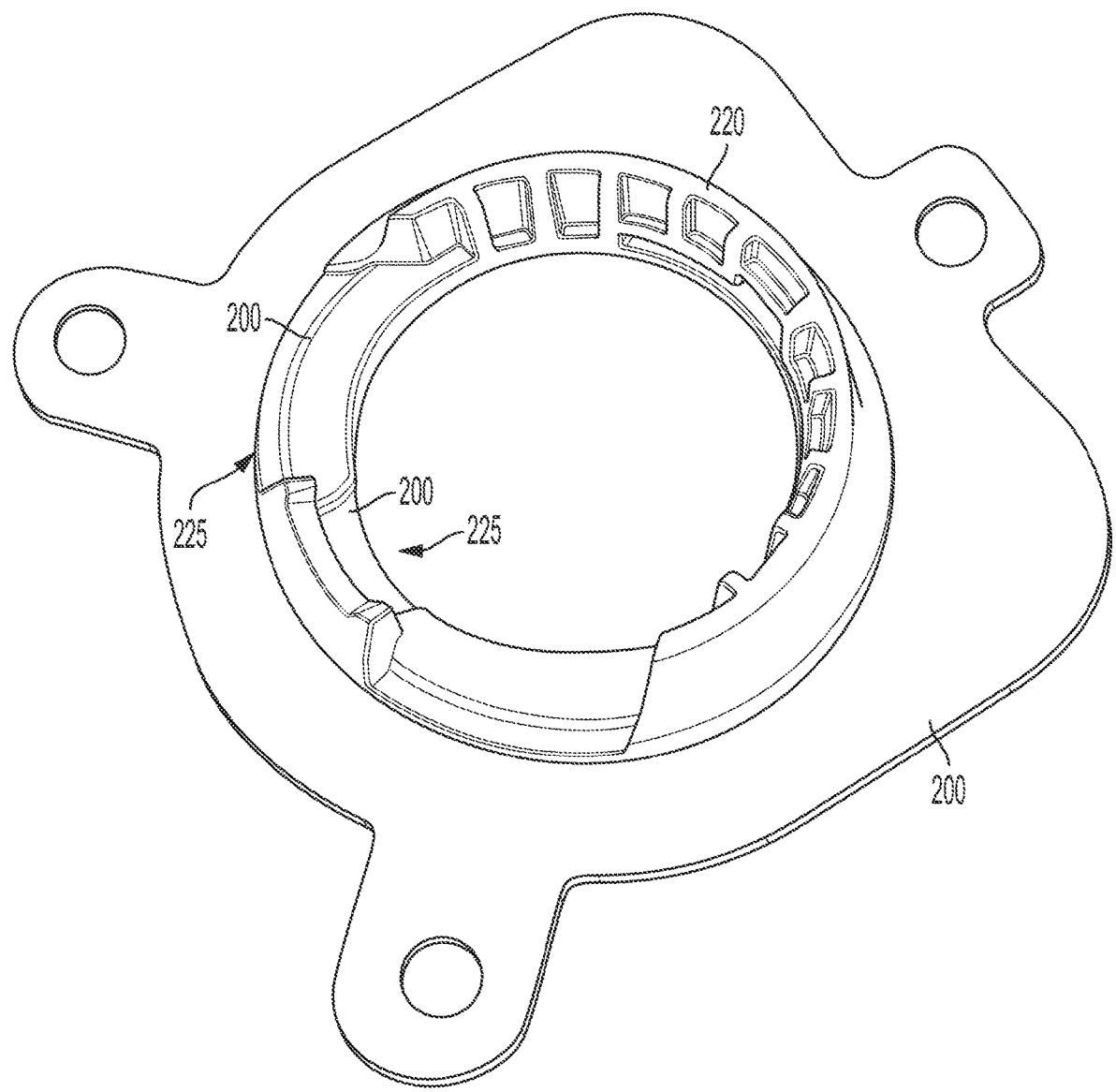
Figure 26:
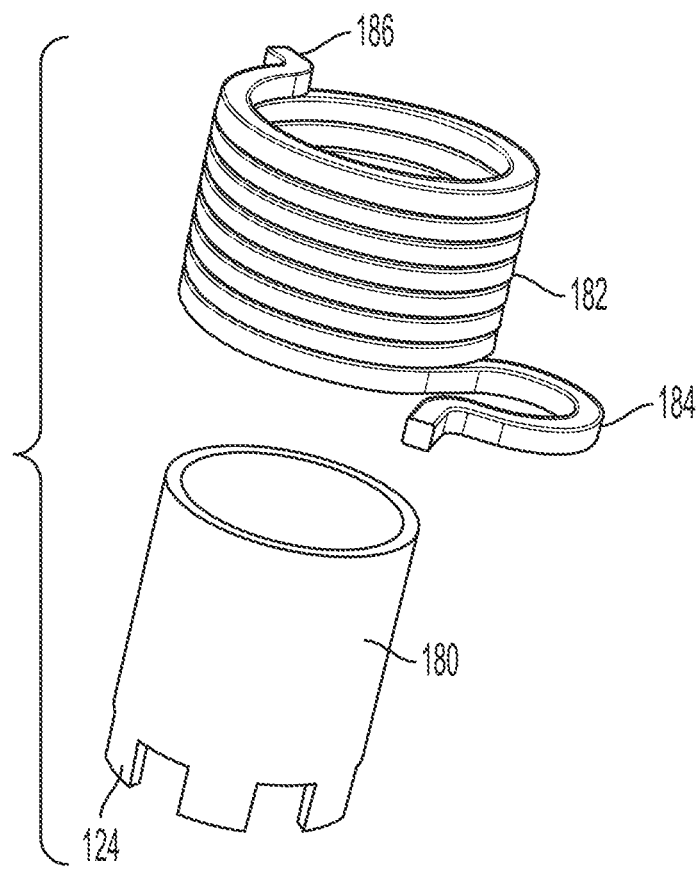
FIGS. 26-30 illustrate an alternative embodiment of a friction based load holding mechanism that may be employed in the reel system of FIG. 1 and that includes a single hub and coil spring.

As shown in FIG. 25, in some embodiments the base member 220 includes one or more thinner material sections 225. Since the fabric 200 is disposed or positioned within the base member's material, the fabric 200 may be visible on a top surface of the thinner material sections 225 of the base member 220. FIG. 23 illustrates a view of the fabric 200 before the base member's material has been injected through the fabric 200. The fabric 200 includes injection holes 226 that are arranged to facilitate in saturation/integration of the polymer material through the fabric 200 to form the annular ring 223 illustrated in FIG. 24. FIG. 23 also illustrates the fabric 200 includes a plurality of tabs 240 that extend laterally outward from a main body of the fabric 200. One or more of the tabs 240 may include an aperture 241 as illustrated.

While the variance of the material saturation/integration within the fabric 200 is shown in relation to the base member 220, it should be realized that other components of the system may likewise be directly injected onto a fabric, such as a guide member for the tension member and other components. Thus, the general description above is related to any reel system component and not specifically to base members.

A method of forming a component of a reel based tensioning system may include providing a fabric material and positioning the fabric material within a die or mold. The method may also include injecting a polymer material through the fabric material so that the polymer material fills a void or space within the die or mold that defines a shape of a first component of the reel based tensioning system. The method may also include cooling the polymer material so that the polymer material hardens and forms the first component of the reel based tensioning system. The polymer material of at least a portion of the first component is saturate or impregnate through the fabric material so that the polymer material of the first component extends axially bellow a bottom surface of the fabric material and axially above a top surface of the fabric material. The fabric material may be positioned within a bottom end of the die or mold so that the polymer material is injected through the fabric material from the bottom end of the die or mold toward a top end of the die or mold. The bottom end of the die or mold may correspond to a bottom end of the first component. The polymer material may be injected through the fabric material and cooled so that the polymer material of an entire bottom end of the first component is saturated or impregnated through the fabric material. In such instances, the polymer material of the entire bottom may extend axially bellow the bottom surface of the fabric material and axially above the top surface of the fabric material. The polymer material may be injected through the fabric material and cooled so that the polymer material forms an annular ring atop the bottom surface of the fabric material. The polymer material may comprise or consists of a glass filled polypropylene material, a co-polyester material, or a combination thereof. The polymer material may be injected through the fabric material and cooled so that the polymer material is visible from a top surface of a materially thinner section or segment of the first component.

Figure 20:
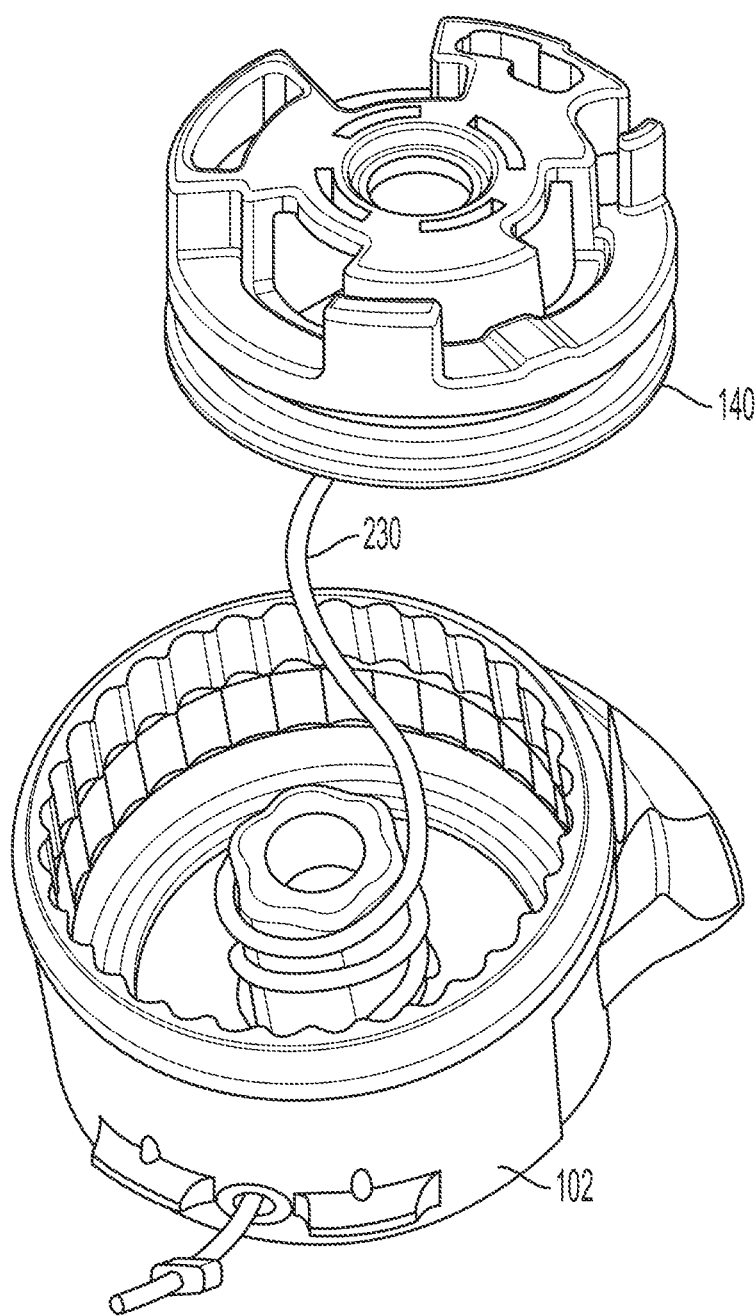
FIG. 20 illustrates a stop cord or mechanism that may be attached to a spool and housing of the reel system of FIG. 1.

Referring now to FIG. 20, illustrated is a stop cord or mechanism 230 that is attached to the spool 140 and the housing 102. The stop cord 230 is wound around a stop cord channel 232 that is separate from the annular channel 144. The stop cord 230 is wrapped around the stop cord channel 232 so that as the tension member is unwound from the annular channel 144, the stop cord 230 wraps around the stop cord channel 232. The length and arrangement of the stop cord 230 and the stop cord channel 232 is such that when the tension member is fully or mostly unwound from the annular channel 144, the stop cord 230 is mostly or fully wrapped around the stop cord channel 232, which prevents further rotation of the spool 140 within the interior region 116 of the housing 102. In this manner, the stop cord 230 prevents back-winding of the tension member about the annular channel 144—i.e., winding of the tension member around the annular channel 144 when the spool is rotated in the loosening direction. The function and arrangement of the stop cord is further described in U.S. Pat. No. 9,259,056, filed Jun. 21, 2013, and entitled "Reel Based Lacing System," the entire disclosure of which is incorporated by reference herein.

To attach the stop cord 230 to the reel system 100, a proximal end of the stop cord 230 is inserted through a coupling aperture 108 in the housing and a knot is tied in the proximal end of the stop cord 230. The knot engages with the coupling aperture 108 to prevent the proximal end of the stop cord 230 from being pulled through the coupling aperture 108. A distal end of the stop cord 230 is similarly inserted through a pair of apertures (not shown) in the spool 140 and a knot is tied in the distal end of the stop cord 230. The knot engages with an uppermost aperture (not shown) to prevent the distal end of the stop cord 230 from being pulled through the spool 140. When the knot in the distal end of the stop cord 230 is engaged with the spool's aperture, the knot is positioned within a slot 109 of the spool 140. In some instances, a small portion of the stop cord 230 extends across the spool's annular channel 144. In such instances, the tension member (not shown) is wound around the stop cord 230.

Figure 21:
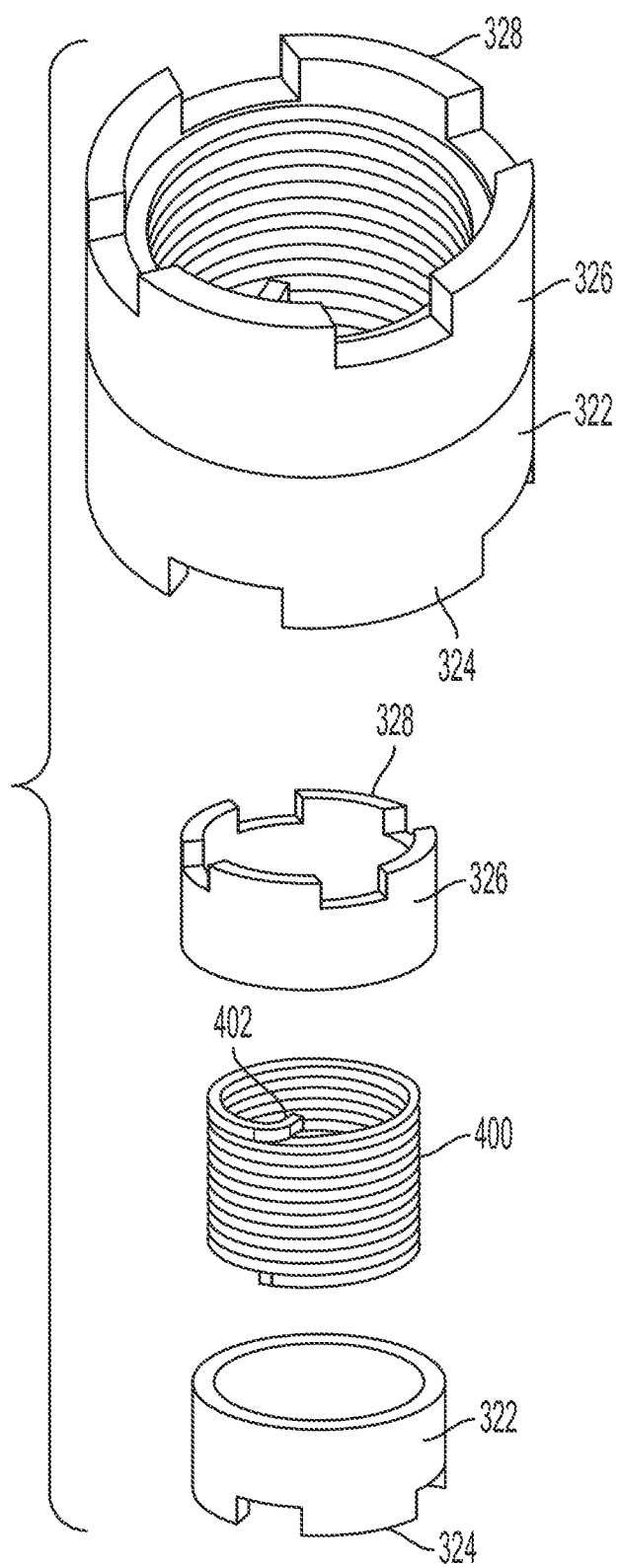
FIGS. 21-22 illustrate an alternative embodiment of a coil spring and release hub assembly that may be employed in the reel system of FIG. 1.
Figure 22:
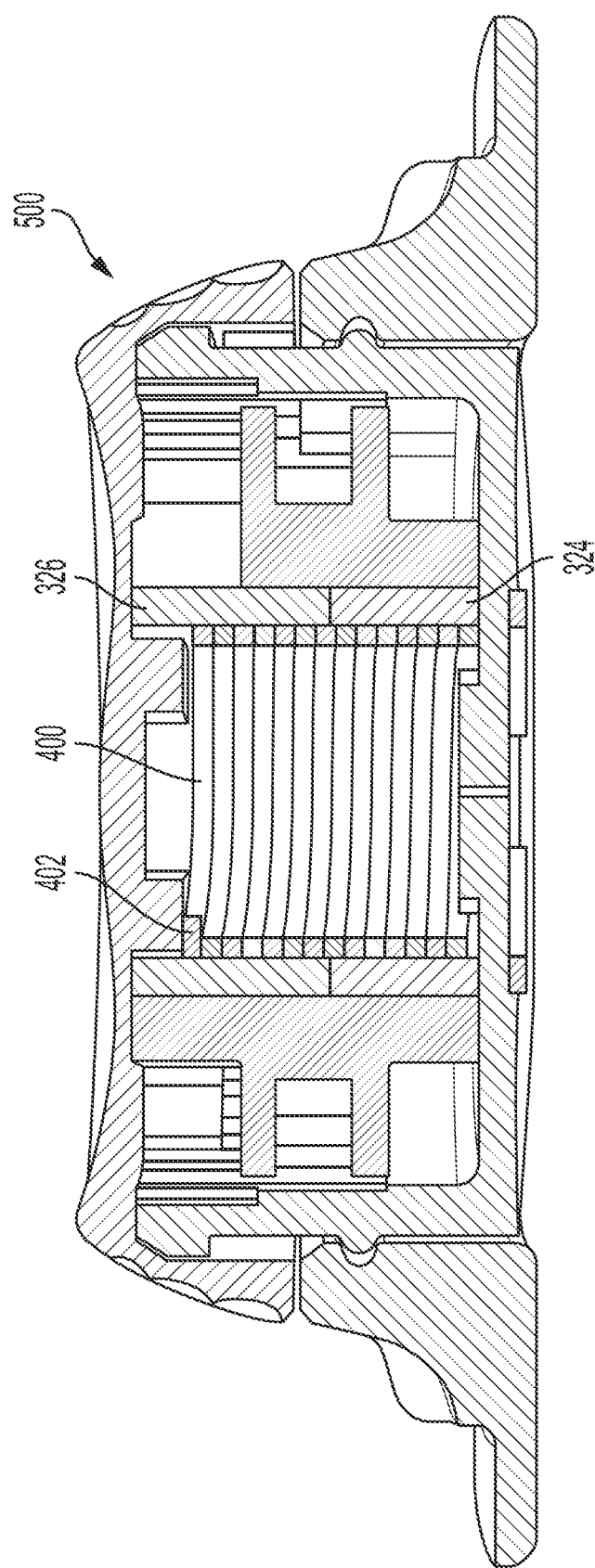

FIGS. 21-22 illustrate an alternative embodiment of a coil spring 400 and release hub assembly. Specifically, the coil spring 400 is configured to be positioned within an upper hub 326 and a lower hub 322. An outer diameter of the coil spring 400 is approximately the same size as or slightly larger than an inner diameter of the upper hub 326 and lower hub 322 so that the spring 400 flexes outward into frictional engagement with the upper hub 326 and the lower hub 322 in order to lock the two hubs together in a manner similar to that described herein. As shown in FIG. 22, the lower hub 322 is fixedly secured to the housing of the reel system 500 via axially extending teeth 324 while the upper hub 326 is fixed to the spool of the reel system 500 via axially extending teeth 328. Locking the upper hub 326 and the lower hub 322 together prevents the upper hub 326 from rotating relative to the lower hub 322, which locks the spool in position relative to the housing.

To unlock the upper hub 326 from the lower hub 322, the diameter of the coil spring 400 is reduced. The coil spring 400 includes a tang 402 that extends radially inward and that engages a release sleeve (not shown) or a component of the knob. As the knob is rotated in a loosening direction, the tang 402 is engaged, via the release sleeve or a component of the knob, which causes the spring coil 400 to be wound in a direction that causes the coil spring to constrict or move radially inward thereby (i.e., a counter-clockwise direction for the spring shown in FIG. 21). Movement of the coil spring 400 in this manner causes the coil spring's outer diameter to decrease to the point where the upper hub 326 is unlocked from the lower hub 322 and is able to rotated relative to the lower hub 322, which allows the spool to rotate within the housing in the loosening direction.

The upper hub 326 and lower hub 322 may have different sized inner diameters, may be made of different materials, and/or may have different surface finishes to ensure that the coil spring 400 is rotatable about one of the hubs while remaining fixed to the other hub as desired. When a release sleeve is employed, the release sleeve may be a cylindrical sleeve that fits entirely within the interior of the coil spring 400 in a manner that minimizes frictional engagement of the release sleeve and coil spring 400. In addition, although the tang 402 is shown positioned near the outer end of the upper hub 326, in other embodiments the tang 402 may be positioned adjacent an outer end of the lower hub 322.

While several embodiments and arrangements of various components are described herein, it should be understood that the various components and/or combination of components described in the various embodiments may be modified, rearranged, changed, adjusted, and the like. For example, the arrangement of components in any of the described embodiments may be adjusted or rearranged and/or the various described components may be employed in any of the embodiments in which they are not currently described or employed. As such, it should be realized that the various embodiments are not limited to the specific arrangement and/or component structures described herein.

In addition, it is to be understood that any workable combination of the features and elements disclosed herein is also considered to be disclosed. Additionally, any time a feature is not discussed with regard in an embodiment in this disclosure, a person of skill in the art is hereby put on notice that some embodiments of the invention may implicitly and specifically exclude such features, thereby providing support for negative claim limitations.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A reel based tensioning device comprising:
  a housing having an interior region;
  a spool rotatably positioned within the interior region of the housing;

a knob operably coupled with the spool to cause the spool to rotate in a first direction within the interior region of the housing to wind a tension member about the spool and thereby tension the tension member; and an audible component that is configured to produce an audible noise in response to operation of the knob to audibly signal an adjustment in tension of the tension member;

wherein the audible component is not configured to prevent rotation of the spool within the housing when a rotational force is imposed on the spool via the tension member or knob.

2. The reel based tensioning device of claim 1, further comprising a load holding mechanism that is separate from the audible component and that is coupled with the spool and configured to allow rotation of the spool in the first direction within the interior region of the housing and to prevent rotation of the spool in a second direction within the interior region of the housing to prevent unwinding of the tension member from about the spool, wherein the load holding mechanism does not produce an audible noise that is detectable by a human.

3. The reel based tensioning device of claim 1, wherein the audible component is configured to produce an audible noise responsive to tensioning of the tension member and to produce an audible noise responsive to loosening of the tension member.

4. The reel based tensioning device of claim 3, wherein the audible noise responsive to tensioning of the tension member is different than the audible noise responsive to loosening of the tension member.

5. The reel based tensioning device of claim 1, wherein the audible component comprises a pawl member or beam that engages with teeth of the housing to produce the audible noise.

6. The reel based tensioning device of claim 1, wherein the audible component is adjustable to adjust the audible noise that is produced by the audible component.

7. The reel based tensioning device of claim 1, wherein the audible component is coupled with a top surface of the spool.

8. A reel based tensioning device comprising:
a housing;
a spool rotatably positioned within the housing;
a knob operably coupled with the spool to cause the spool to rotate in a first direction within the housing to wind a tension member about the spool; and
an audible component that is configured to produce an audible noise responsive to operation of the knob to signal an adjustment of the tension member;
wherein the audible component is not configured to prevent rotation of the spool within the housing when an appreciable rotational force is imposed on the spool via the tension member or knob.

9. The reel based tensioning device of claim 8, further comprising a load holding mechanism coupled with the spool and configured to allow rotation of the spool in the first direction within the housing and to prevent rotation of the spool in a second direction within the housing to prevent unwinding of the tension member from about the spool.

10. The reel based tensioning device of claim 8, wherein the audible component is configured to produce an audible noise responsive to tensioning of the tension member and to produce an audible noise responsive to loosening of the tension member.

11. The reel based tensioning device of claim 10, wherein the audible noise responsive to tensioning of the tension member is different than the audible noise responsive to loosening of the tension member.

12. The reel based tensioning device of claim 8, wherein the audible component comprises a pawl member or beam.

13. The reel based tensioning device of claim 8, wherein the audible component is coupled with a top surface of the spool.

14. The reel based tensioning device of claim 8, wherein the audible component is adjustable to adjust the audible noise that is produced by the audible component.

15. A method of configuring a reel based tensioning device comprising:
providing the reel based tensioning device, the reel based tensioning device including:
a housing;
a spool rotatably positioned within the housing; and
a knob operably coupled with the spool to cause the spool to rotate in a first direction within the housing to wind a tension member about the spool; and
coupling an audible component with the reel based tensioning device;
wherein the audible component is configured to produce an audible noise responsive to operation of the knob to signal an adjustment of the tension member; and
wherein the audible component is not configured to prevent rotation of the spool within the housing when an appreciable rotational force is imposed on the spool via the tension member or knob.

16. The method of claim 15, wherein the reel based tensioning device also includes a load holding mechanism coupled with the spool and configured to allow rotation of the spool in the first direction within the housing and to prevent rotation of the spool in a second direction within the housing to prevent unwinding of the tension member from about the spool.

17. The method of claim 15, wherein the audible component is configured to produce an audible noise responsive to tensioning of the tension member and to produce an audible noise responsive to loosening of the tension member.

18. The method of claim 17, wherein the audible noise responsive to tensioning of the tension member is different than the audible noise responsive to loosening of the tension member.

19. The method of claim 15, wherein the audible component comprises a pawl member or beam that engages with the housing to produce the audible noise.

20. The method of claim 15, further comprising adjusting the audible component to adjust the audible noise that is produced by the audible component.

\* \* \* \* \*